(12) United States Patent
Thompson et al.

(10) Patent No.: US 10,426,941 B2
(45) Date of Patent: Oct. 1, 2019

(54) NASAL TUBE DEVICE AND METHOD

(71) Applicant: Applied Medical Technology, Inc., Brecksville, OH (US)

(72) Inventors: Matthew Thompson, Broadview Hts., OH (US); Dawn Thompson, Broadview Hts., OH (US); George Picha, Brecksville, OH (US); Allison Slaga, Brecksville, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 965 days.

(21) Appl. No.: 13/839,012

(22) Filed: Mar. 15, 2013

(65) Prior Publication Data
US 2013/0338521 A1  Dec. 19, 2013

Related U.S. Application Data

(60) Provisional application No. 61/740,848, filed on Dec. 21, 2012, provisional application No. 61/661,148, filed on Jun. 18, 2012.

(51) Int. Cl.
*A61M 39/08* (2006.01)
*A61M 16/04* (2006.01)
(Continued)

(52) U.S. Cl.
CPC ............ *A61M 39/08* (2013.01); *A61B 5/082* (2013.01); *A61B 5/6852* (2013.01);
(Continued)

(58) Field of Classification Search
CPC ............ A61B 2017/1785; A61B 17/24; A61B 2017/246; A61B 1/233; A61B 5/6852;
(Continued)

(56) References Cited

U.S. PATENT DOCUMENTS 3,420,237 A * 1/1969 Fortay .............. A61B 17/12022
604/11
3,568,678 A  3/1971 Pourquier et al.
(Continued)

FOREIGN PATENT DOCUMENTS

FR  1336296 A  8/1963
JP  2004508108 A  3/2004
(Continued)

OTHER PUBLICATIONS

Definition of "lumen", www.Merriam-Webster.com/dictionary/lumen. Captured on Dec. 17, 2018.*
(Continued)

*Primary Examiner* — Tu A Vo
(74) *Attorney, Agent, or Firm* — Pearne & Gordon, LLP

(57) ABSTRACT

The present application describes nasal tube devices, methods for placing and securing a nasal tube to a patient, as well as adapters and connectors for a nasal tube. In one exemplary embodiment, the nasal tube has a proximal portion, a distal portion, and one or more lumens. A securing device may be attached to the proximal portion of the nasal tube and may be configured to attach a flexible line of a retention system to the nasal tube. The securing device may also be configured to selectively compress the proximal portion of the nasal tube. In certain embodiments, one or more medical tubes are disposed in the lumen of the nasal tube and may be selectively secured in the lumen with the securing device. The nasal tube device may also have a retention flange for attaching a flexible line of a retention system to the nasal tube.

22 Claims, 24 Drawing Sheets

(51) Int. Cl.

| | | |
|---|---|---|
| *A61B 5/08* | (2006.01) | |
| *A61M 16/06* | (2006.01) | |
| *A61B 5/00* | (2006.01) | |
| *A61M 16/08* | (2006.01) | |
| A61B 5/0205 | (2006.01) | |
| A61B 5/083 | (2006.01) | |
| A61M 16/10 | (2006.01) | |

(52) U.S. Cl.
CPC .... *A61M 16/0461* (2013.01); *A61M 16/0488* (2013.01); *A61M 16/0666* (2013.01); *A61M 16/0683* (2013.01); *A61M 16/085* (2014.02); *A61M 16/0816* (2013.01); *A61B 5/02055* (2013.01); *A61B 5/0836* (2013.01); *A61B 2505/05* (2013.01); *A61M 2016/103* (2013.01); *A61M 2016/1025* (2013.01); *A61M 2016/1035* (2013.01); *A61M 2202/0208* (2013.01); *A61M 2210/0618* (2013.01); *A61M 2230/432* (2013.01); *A61M 2230/435* (2013.01); *A61M 2230/437* (2013.01)

(58) Field of Classification Search
CPC .............. A61M 16/00; A61M 16/0461; A61M 16/0666; A61M 16/0672; A61M 16/0683; A61M 16/0688; A61M 16/0694; A61M 2210/0618; A61M 39/08; A61M 16/085; A61M 16/0816; A61M 2230/204; A61M 2202/0208; A61M 2016/103
See application file for complete search history.

(56) References Cited

U.S. PATENT DOCUMENTS

| | | | | |
|---|---|---|---|---|
| 3,776,222 | A * | 12/1973 | Smiddy ................ | A61B 1/0056 385/117 |
| 4,778,448 | A * | 10/1988 | Meer .................... | A61J 15/0053 128/207.18 |
| 4,821,715 | A * | 4/1989 | Downing .......... | A61M 16/0461 128/200.26 |
| 4,932,943 | A * | 6/1990 | Nowak ................. | A61M 25/02 128/DIG. 26 |
| 5,097,827 | A | 3/1992 | Izumi | |
| 5,185,005 | A | 2/1993 | Ballantyne | |
| 5,492,538 | A * | 2/1996 | Johlin, Jr. ......... | A61M 25/0068 128/899 |
| 5,692,506 | A * | 12/1997 | Linder .............. | A61M 25/0068 600/380 |
| 5,752,511 | A | 5/1998 | Simmons | |
| 5,937,858 | A | 8/1999 | Connell | |
| 6,098,617 | A * | 8/2000 | Connell ................. | A61M 16/04 128/200.26 |
| 6,159,158 | A | 12/2000 | Lowe | |
| 6,173,199 | B1 | 1/2001 | Gabriel | |
| 6,266,547 | B1 * | 7/2001 | Walker ................. | A61B 5/0088 600/323 |
| 6,394,093 | B1 * | 5/2002 | Lethi ................ | A61M 16/0461 128/207.13 |
| 6,408,850 | B1 * | 6/2002 | Sudge ............. | A61M 16/0488 128/207.14 |
| 6,464,668 | B1 | 10/2002 | Pace | |
| 6,488,664 | B1 | 12/2002 | Solomon et al. | |
| 6,631,715 | B2 | 10/2003 | Kirn | |
| 6,837,237 | B2 | 1/2005 | Kirn | |
| 7,534,228 | B2 | 5/2009 | Williams | |
| 7,604,627 | B2 * | 10/2009 | Kojouri ............. | A61M 25/0068 604/516 |
| 8,020,558 | B2 * | 9/2011 | Christopher ...... | A61M 16/0051 128/200.24 |
| 8,056,562 | B2 | 11/2011 | Sherman | |
| 2002/0026936 | A1 | 3/2002 | Kirn | |
| 2004/0069309 | A1 | 4/2004 | Kirn | |
| 2004/0099273 | A1 * | 5/2004 | Wright .............. | A61M 16/0084 128/207.18 |
| 2004/0231675 | A1 | 11/2004 | Lyons | |
| 2005/0236001 | A1 | 10/2005 | Williams | |
| 2005/0240147 | A1 * | 10/2005 | Makower ............... | A61B 17/24 604/96.01 |
| 2006/0283464 | A1 * | 12/2006 | Dunlap ............. | A61M 16/0461 128/207.18 |
| 2008/0006275 | A1 | 1/2008 | Nickelson et al. | |
| 2008/0071249 | A1 * | 3/2008 | Vadivelu ........... | A61M 16/0463 604/540 |
| 2008/0142019 | A1 | 6/2008 | Lewis et al. | |
| 2009/0151719 | A1 * | 6/2009 | Wondka ............ | A61M 16/0051 128/203.12 |
| 2009/0156953 | A1 * | 6/2009 | Wondka ............ | A61M 16/0465 600/538 |
| 2009/0248057 | A1 * | 10/2009 | Kotler ............... | A61M 16/0666 606/199 |
| 2010/0242967 | A1 * | 9/2010 | Burbank ................. | A61F 5/56 128/207.18 |
| 2012/0080037 | A1 * | 4/2012 | Guyuron ........... | A61M 16/0461 128/207.18 |
| 2012/0168571 | A1 * | 7/2012 | Bond ................. | A61M 16/0488 248/70 |
| 2013/0019872 | A1 * | 1/2013 | Guyuron .......... | A61M 16/0461 128/207.18 |
| 2013/0087152 | A1 * | 4/2013 | Kirn .................. | A61M 16/0488 128/207.14 |
| 2013/0152940 | A1 * | 6/2013 | Larson .............. | A61M 16/0461 128/207.18 |

FOREIGN PATENT DOCUMENTS

| | | |
|---|---|---|
| WO | 9920344 | 4/1999 |
| WO | 99/29358 A1 | 6/1999 |
| WO | 2002020082 | 3/2002 |

OTHER PUBLICATIONS

Dominguez, E., "Carbon Dioxide Monitoring during Deep Conscious Sedation . . . ," Anesthesiology 1999, vol. 91, No. 4, pp. 1177-1178, Oct. 1999.
Dominguez, E., "Another Use for Nasopharyngeal Airway," Anesthesiology 2000, vol. 93, No. 1, pp. 298-299, Jul. 2000.
Lee, Christopher R., "Who Nose Where the Airway Is?", Agency for Healthcare Research and Quality (AHRQ) WebM&M, Cases & Commentary, Oct. 2009. http://www.webmm.ahrq.gov.
AMT Bridle Nasal Tube Retaining System brochure, 4 pgs., Applied Medical Technology, Inc., copyright 2010. www.appliedmedical.net.
Kotler, R., et al., "Introducing . . . The Kotler Nasal Airway™", The Kotler Nasal Airway Official Website, "A Strategy and New Device to Ensure Patient Safety . . . ," copyright 2011. www.kotlernasalairway.com.
International Search Report and Written Opinion from PCT/US2013/046213, dated Oct. 21, 2013.
Rhino Rocket® with Applicator, Shipped Medical Technologies Incorporated on-line catalog, vol. IX, p. 11, copyright 2013. www.shippertmedical.com.
Rapid Rino® 900, ArthroCare Corporation, on-line Technique Guide, 2 pgs., copyright 2009. www.arthrocareENT.com.
Extended European Search Report from European Patent Application No. 13807038.8 dated May 18, 2016.
Levenson, Albert, "Feeding Tube Anchor," 5 Nutritional Support Services, 8, pp. 40-42 (1985).
Barrocas, Albert, "The Bridle:Increasing the Use of Nasoenteric Feedings," Nutritional Support Services, vol. 2, No. 8, Aug. 1982, pp. 8-10.
McGuirt, W. Frederick et al., "Securing of Intermediate Duration Feeding Tubes" The Laryngoscope 90:1980, pp. 2046-2048.
Meer, Jeffrey A., A New Nasal Bridle for Securing Nasoentereal Feeding Tubes, 13 J. Parenteral & Enteral Nutrition, 331, 331-33 (1989).

(56) References Cited

OTHER PUBLICATIONS

English translation of Notice of Reasons for Rejection for Japanese Patent Application No. 2015-526757 dated Jun. 1, 2017.

* cited by examiner

NASAL TUBE DEVICE AND METHOD

CROSS REFERENCE TO RELATED APPLICATIONS

This application is a U.S. Non-Provisional Patent Application which claims priority to U.S. Provisional Patent Application No. 61/661,148, filed on Jun. 18, 2012 and titled "Nasal Tube Device and Method," and U.S. Provisional Patent Application No. 61/740,848, filed on Dec. 21, 2012 and titled "Medical Tube," both of which are hereby incorporated by reference in their entirety.

BACKGROUND

There are a number of types of nasal tubes used in medicine to treat various conditions. These nasal tubes generally enter through a nostril and travel within the pharyngeal spaces of the patient to their respective destinations. The travel path, destination, tube termination, and function of the nasal tube may vary. For example, a nasogastic tube enters through the nose, terminates in the gut-tube pathway, and delivers nutrients for digestion. A nasopharyngeal airway, also known as an NPA or a nasal trumpet, enters through the nose, terminates near the laryngopharynx, and creates a passive patent airway. A nasotracheal tube enters through the nose, is secured by a balloon, terminates just superior to the tracheal bifurcation, and creates a definitive airway capable of positive pressure ventilation. That same tube, however, may facilitate the passage of cameras and other medical tools thus serving as a protective port during a medical procedure as opposed to an airway.

Nasal tubes are often secured to the patient to prohibit removal or displacement of the tube. Serious and expensive medical complications can result from the unintentional removal or displacement of a nasal tube. Displacement of a tube, especially at its terminus, without an obvious tube pullout is especially harmful as it may go unrecognized by caregivers. Furthermore, nasal catheters are often used to monitor patients under general anesthesia. For example, nasal catheters are generally inserted through the nose of the patient and terminate in the nasopharyngeal space to deliver oxygen to the patient or monitor the patient's expiration of carbon dioxide during surgery. In the US, the American Society of Anesthesiologists (ASA) have established minimum monitoring guidelines for patients receiving general anesthesia, regional anesthesia, or sedation. This includes electrocardiography (ECG), heart rate, blood pressure, inspired and expired gases (e.g., oxygen, carbon dioxide, or inhalational anesthetic agents), oxygen saturation of the blood (pulse oximetry), and temperature.

SUMMARY

The present application discloses nasal tube devices, methods for placing and securing a nasal tube to a patient, as well as adapters and connectors for a nasal tube.

In certain exemplary embodiments, the nasal tube device comprises a nasal tube having a proximal portion, a distal portion, and one or more lumens. A securing device is attached to the proximal portion of the nasal tube and is configured to attach a flexible line of a retention system to the nasal tube.

In certain exemplary embodiments, the nasal tube device comprises a nasal tube having a proximal portion, a distal portion, a retention flange, and one or more lumens The retention flange comprises one or more openings for attaching a flexible line of a retention system to the nasal tube.

In certain exemplary embodiments, the method of placing and securing a nasal tube to a patient comprises utilizing a nasal tube device having a nasal tube attached to a retention system. The retention system comprises a flexible line attached to the nasal tube. The flexible line is pulled around the vomer bone of a patient. The distal end of the nasal tube is simultaneously inserted into a first nostril of the patient as the flexible line is being pulled around the vomer bone. The distal end of the nasal tube is positioned in a pharyngeal space of the patient. The flexible line is secured around the vomer bone by attaching the flexible line to a proximal portion of the nasal tube.

In certain exemplary embodiments, the nasal tube device comprises a nasal tube having a proximal portion, a distal portion, and a delivery lumen extending from the proximal portion to an opening in the outer surface of the nasal tube. The delivery lumen is configured to receive a connector attached to a flexible line of a retention system.

In certain exemplary embodiments, the method of placing and securing a nasal tube to a patient comprises utilizing a nasal tube device comprising a nasal tube having a proximal portion, a distal portion, and a delivery lumen extending from the proximal portion to a delivery window. The delivery lumen is configured to receive a connector attached to a flexible line of a retention system. The distal end of the nasal tube is inserted into a first nostril of a patient and positioned in a pharyngeal space of the patient. The connector attached to the flexible line is deployed out the delivery window. The flexible line is pulled through the delivery lumen, around the vomer bone of the patient, and out the second nostril of the patient. The flexible line is secured around the vomer bone by attaching the flexible line to the proximal portion of the nasal tube.

In certain exemplary embodiments, the adapter for a nasal tube comprises a first end having a first port and a second port. Each of the first and second ports of the first end are configured for receipt in a lumen of a nasal tube. A second end of the adapter has a first port in fluid communication with the first port of the first end and a second port in fluid communication with the second port of the first end. Each of the first and second ports of the second end are configured for removable connection to a medical tube.

In certain exemplary embodiments, the nasal tube device comprises a nasal tube having a proximal portion, a distal portion, and a lumen extending from the proximal portion to the distal portion of the nasal tube. A securing device is attached to the proximal portion of the nasal tube. The securing device is configured to selectively compress the proximal portion of the nasal tube. One or more medical tubes are disposed in the lumen of the nasal tube. The one or more medical tubes are selectively secured in the lumen with the securing device.

These and additional embodiments will become apparent in the course of the following detailed description.

BRIEF DESCRIPTION OF DRAWINGS

In the accompanying drawings which are incorporated in and constitute a part of the specification, embodiments of the invention are illustrated, which, together with a general description of the invention given above, and the detailed description given below, serve to example the principles of the inventions.

DETAILED DESCRIPTION OF EMBODIMENTS

Figure 1A:
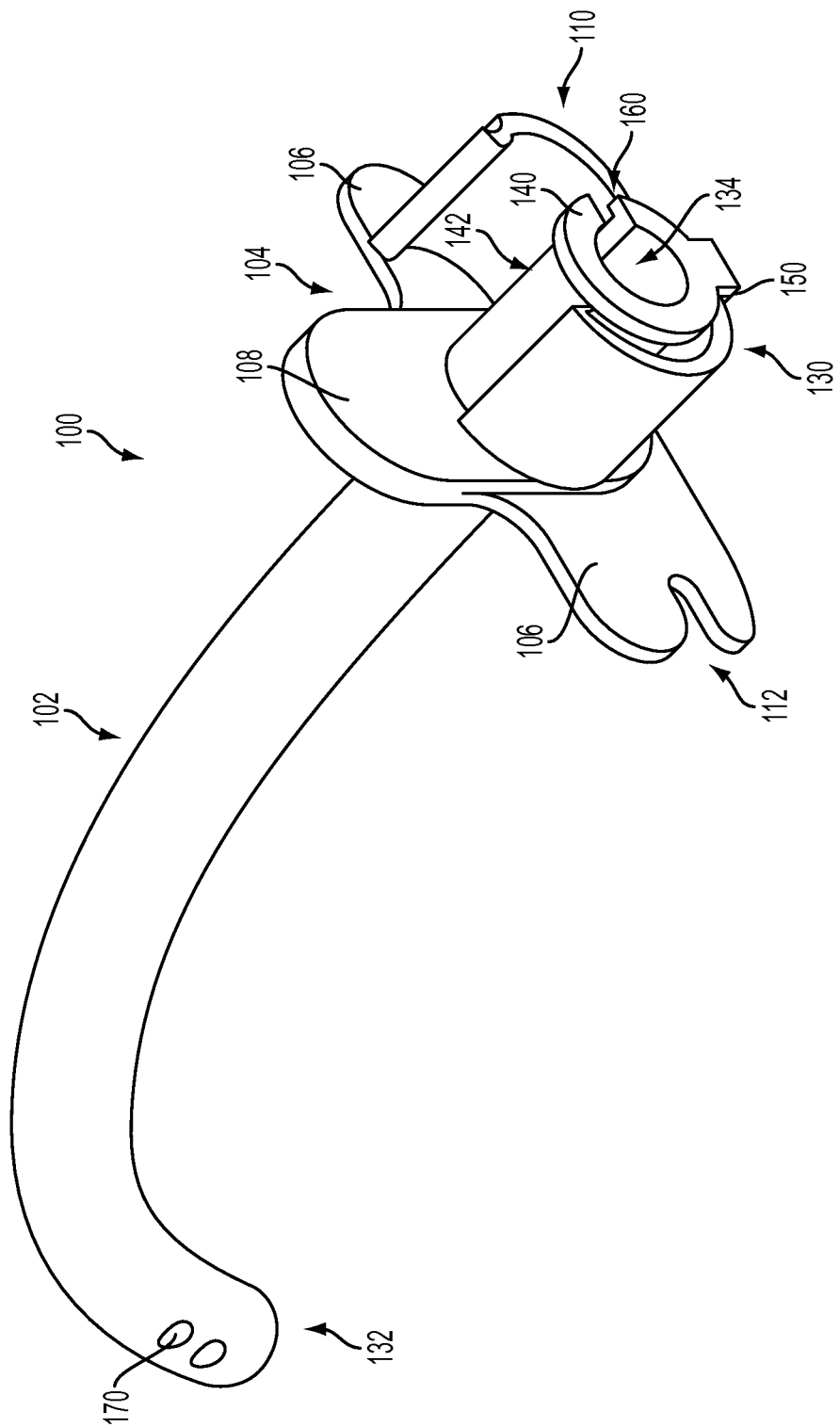
FIG. 1A is a perspective view of a nasal tube device according to an embodiment of the present application, wherein a securing device of the nasal tube device is in an open position.

The present application discloses nasal tube devices. As used herein, "nasal tube" includes any tube that may be inserted through the nose of a patient for a medical purpose. For example, a nasal tube device of the present application may be used as a secure nasal tube for airway management, an anesthesiology monitoring device, a delivery port for medical tubes, wires, or instruments, and/or an oxygen delivery device. The present application also discloses methods for placing and securing a nasal tube to a patient, as well as adapters and connectors for a nasal tube.

The nasal tube device of the present application may include a variety of nasal tube types for nearly any medical purpose. For example, the nasal tube may be designed to terminate in the pharyngeal spaces of the patient, such as the oropharyngeal or largyngopharyngeal space of the patient. As another example, the nasal tube may be designed to extend into the esophagus of the patient and terminate in the alimentary tract to aid in nutrient delivery, drug delivery, endoscopy, decompression, etc. The nasal tube may also be designed to terminate in the bronchi or the lungs. Further, the nasal tube may be a variety of sizes for various applications, such as biopsy in both adult and pediatric populations. In some embodiments, the nasal tube may be fitted with an inflatable balloon at or near its distal end to facilitate retention of the nasal tube in the patient. Further, the inflatable balloon may be configured to move the tongue away from the distal end of the nasal tube and/or prohibit obstruction of the nasal tube.

The nasal tube device of the present application may also comprise multiple lumens and/or may bifurcate and pass simultaneously into the esophagus and trachea. Further, the nasal tube device may be capable of passing liquids, air, drugs, or medical instruments, in addition to the delivery of a retention system. The nasal tube device may also function as an aid to monitor conscious sedation anesthesia. The nasal tube device may function passively as a secure nasopharyngeal airway for emergencies or as a part of haemostatic post-op care to maintain airway patency. Further, the nasal tube device may be used to deliver positive pressure ventilation.

In certain embodiments, the nasal tube device of the present application comprises a combined nasal tube and nasal tube retention system. For example, in some embodiments, at least a portion of the retention system is attached to the nasal tube to facilitate placement and securement of the nasal tube to the patient. Further, in some embodiments, the nasal tube is configured to deliver at least a portion of the retention system into the appropriate pharyngeal space to secure the nasal tube to the patient.

The nasal tube device of the present application provides numerous advantages over a separate nasal tube and retention systems. For example, the speed of the overall procedure to establish a secure nasal tube is increased by using the nasal tube device. This is particularly important when a patient's airway is compromised, but also has implications for patient comfort as well as ease of the procedure. Further, a combined nasal tube and nasal tube retention system decreases insult from insertion devices. For example, with fewer devices and decreased procedural time, tissue trauma and irritation associated with nasal tube and retention system placement is reduced. Additionally, fewer device insertions correlate with fewer potential procedural failure modes.

In certain embodiments, the nasal tube device of the present application is configured to be used as a secure nasal tube for airway management. The nasal tube device may comprise a nasal tube that terminates in the nasopharyngeal space of the patient. In one embodiment, the nasal tube comprises a plurality of lumens. A first lumen is configured to provide a secure passive airway for the patient and a second lumen is configured to deliver at least a portion of a retention system into the appropriate pharyngeal space to secure the nasal tube to the patient. The nasal tube may also comprise one or more other lumens. Further, in some embodiments, one or more lumens of the nasal tube may be configured to pass liquids, air, drugs, or medical instruments. For example, one or more lumens of the nasal tube may be configured to deliver oxygen to the patient or monitor the patient's expiration of carbon dioxide. As such, the nasal tube device may be configured as a combined secure nasal tube for airway management and anesthesiology monitoring/oxygen delivery device.

In certain embodiments, the nasal tube device of the present application is configured to be used as an anesthesiology monitoring/oxygen delivery device. The nasal tube device comprises a nasal tube that terminates in the nasopharyngeal space of the patient. The nasal tube has a plurality of medical tubes secured within a lumen of the nasal tube. For example, a first tube may be configured to deliver oxygen to the patient and a second tube may be configured for physiological monitoring of the patient, such as, for example, sampling or monitoring inspired or expired gases (e.g., oxygen, carbon dioxide, or inhalational anesthetic agents) or oxygen saturation of the blood. In certain embodiments, the nasal tube may comprise a delivery lumen configured to deliver at least a portion of a nasal tube retention system into the appropriate pharyngeal space to secure the nasal tube to the patient.

Figure 1B:
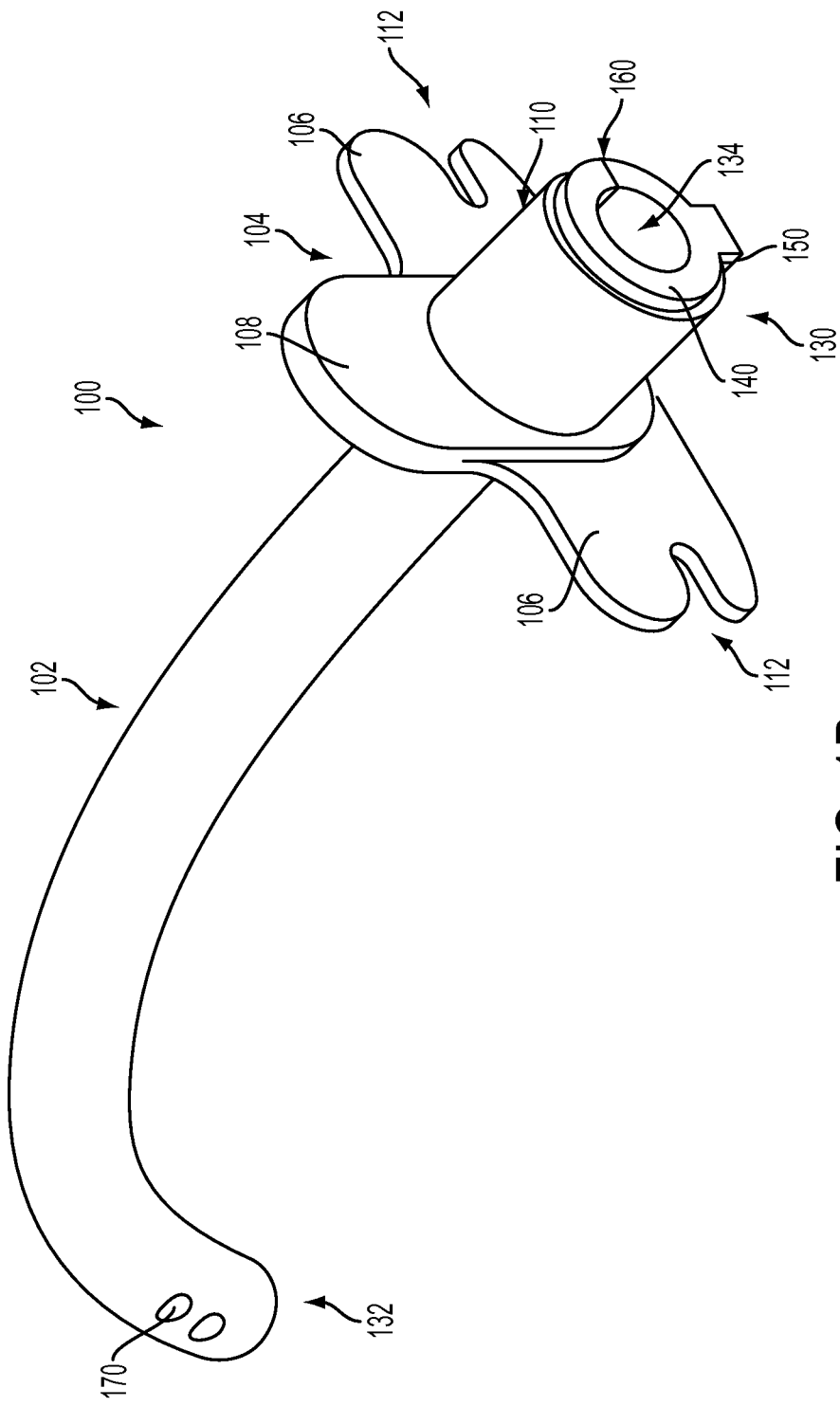
FIG. 1B is a perspective view of the nasal tube device of FIG. 1A, wherein the securing device of the nasal tube device is in a closed position.
Figure 1C:
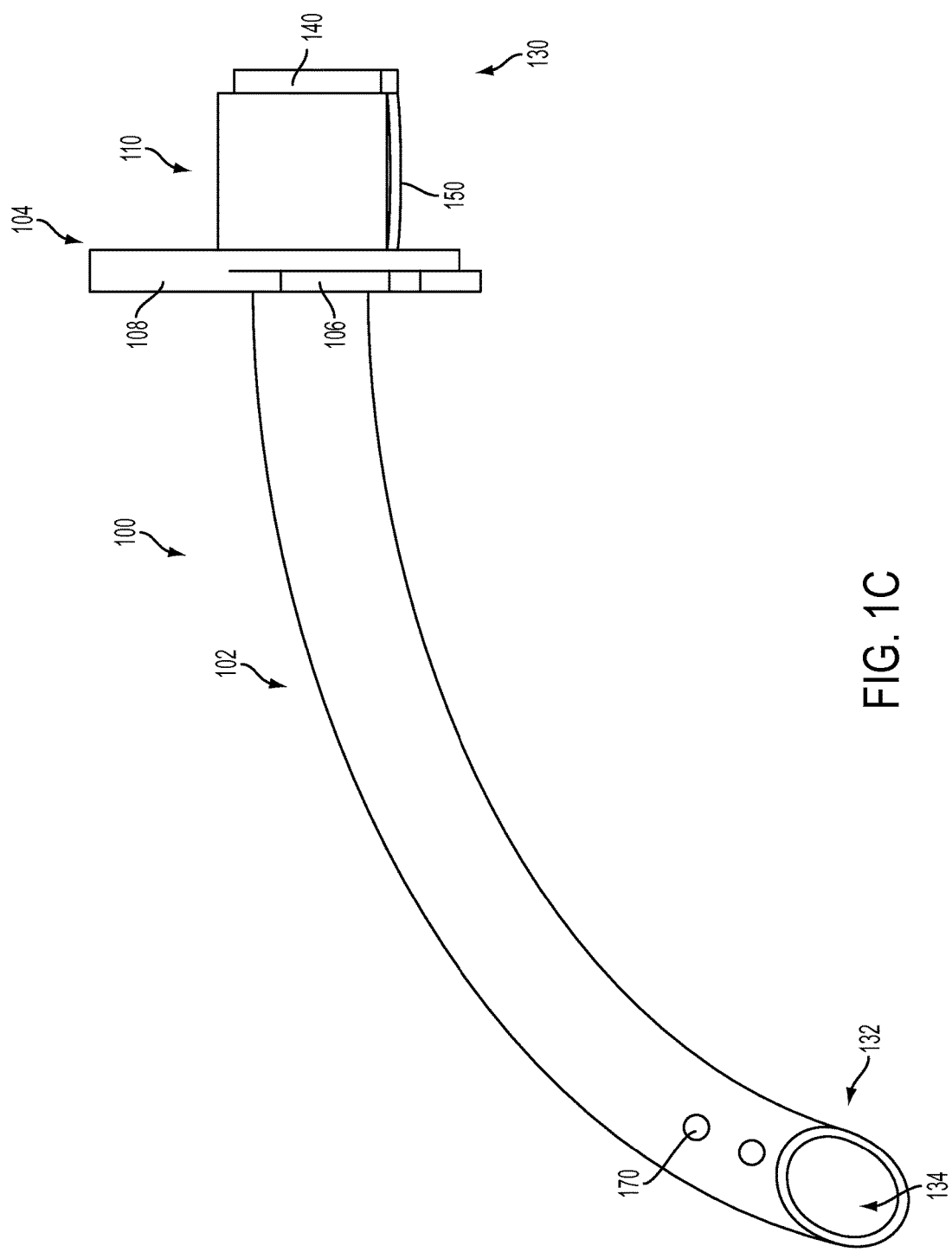
FIG. 1C is a side view of the nasal tube device of FIG. 1A.
Figure 1D:
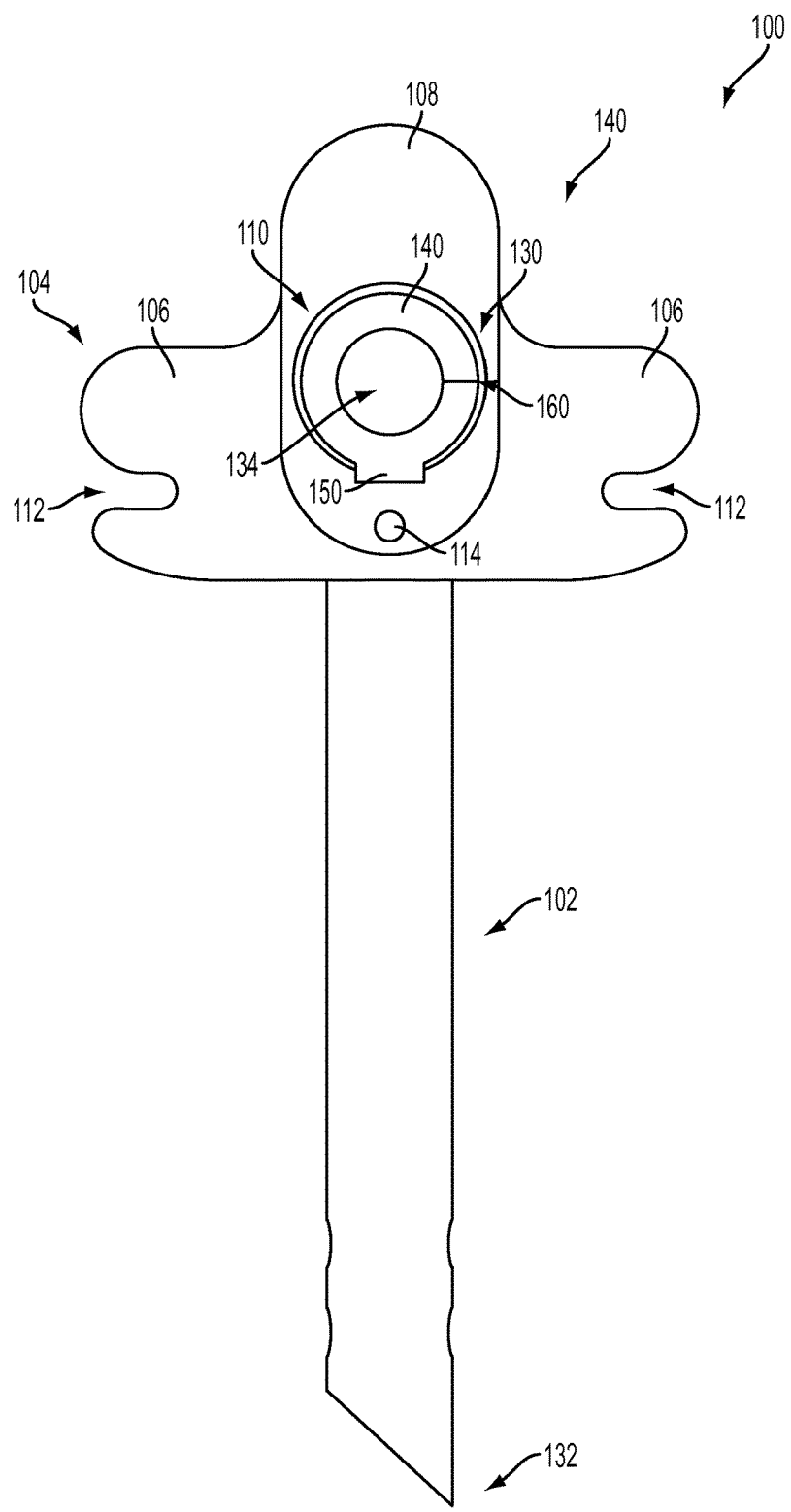
FIG. 1D is a front view of the nasal tube device of FIG. 1A.
Figure 2A:
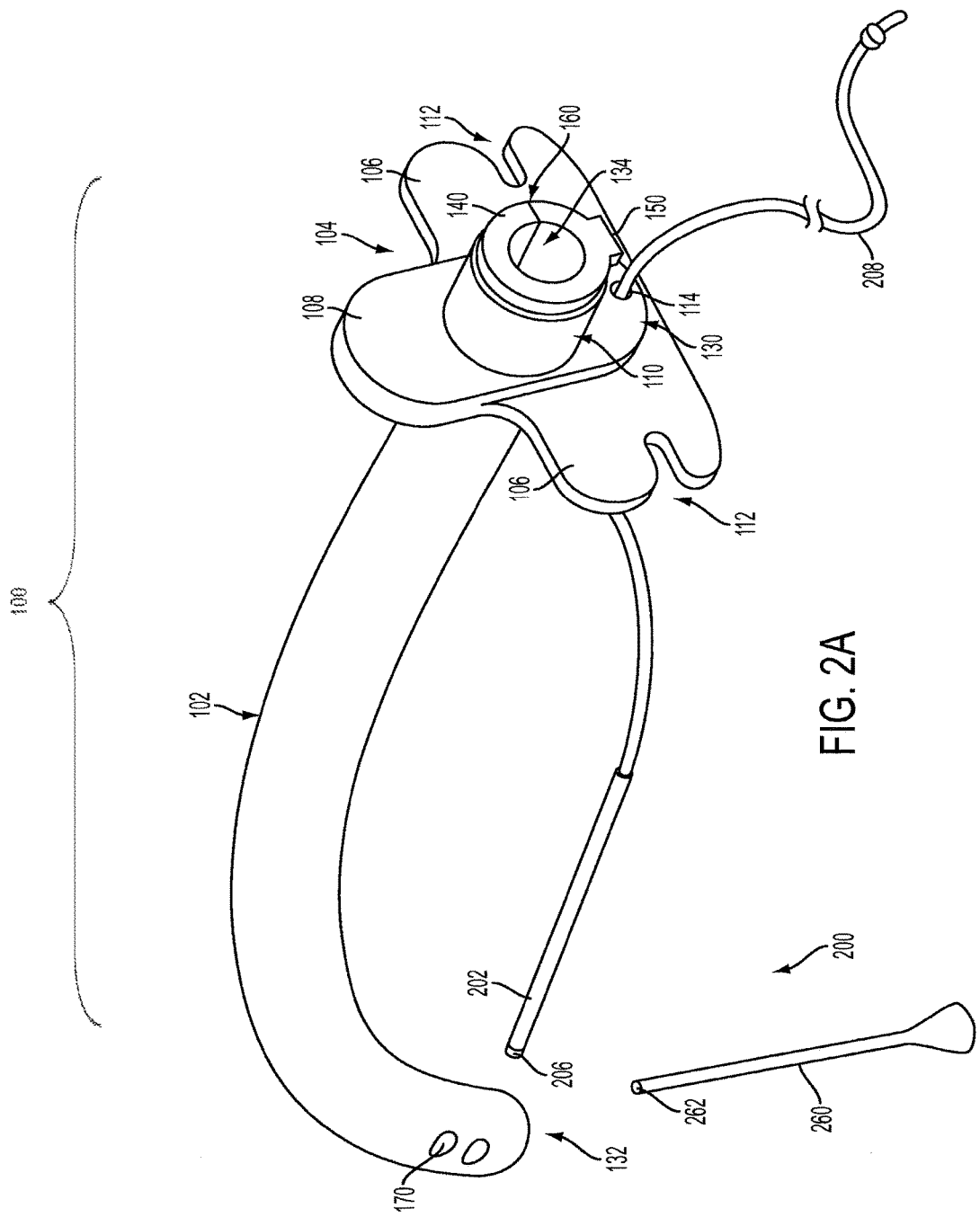
FIGS. 2A-2C are perspective views of the nasal tube device of FIG. 1A, wherein the nasal tube device is attached to a retention system according embodiments of the present application.

FIGS. 1A-1D illustrate a nasal tube device 100 according to an embodiment of the present application. The nasal tube device 100 comprises a nasal tube 102, a retention flange 104, and a securing device 110. The nasal tube 102 forms the body of the device 100 and has a proximal end 130 and a distal end 132. As shown, the nasal tube 102 comprises a single lumen 134 extending from the proximal end 130 to the distal end 132 of the tube. However, in other embodiments, the nasal tube 102 may comprise a plurality of lumens, e.g., one, two, three, four or more lumens, that may or may not extend from the proximal end 130 to the distal end 132 of the nasal tube. FIGS. 2A-3 illustrate the nasal tube device 100 attached to an exemplary retention system 200. The retention system 200 comprises a bridle line 208, a catheter 202 having a first connector 206 at a distal end, and a connecting member 260 having a second connector 262 at a distal end. The bridle line 208 is attached to the catheter 202 and the nasal tube device 100. The first and second connectors 206 and 262 may be a variety of devices or fasteners configured to connect or otherwise attach together, e.g., when touched together or when placed in close proximity to one another. For example, in certain embodiments, the first and second connectors 206 and 262 are magnets that attach together when placed in proximity to one another.

Figure 2B:
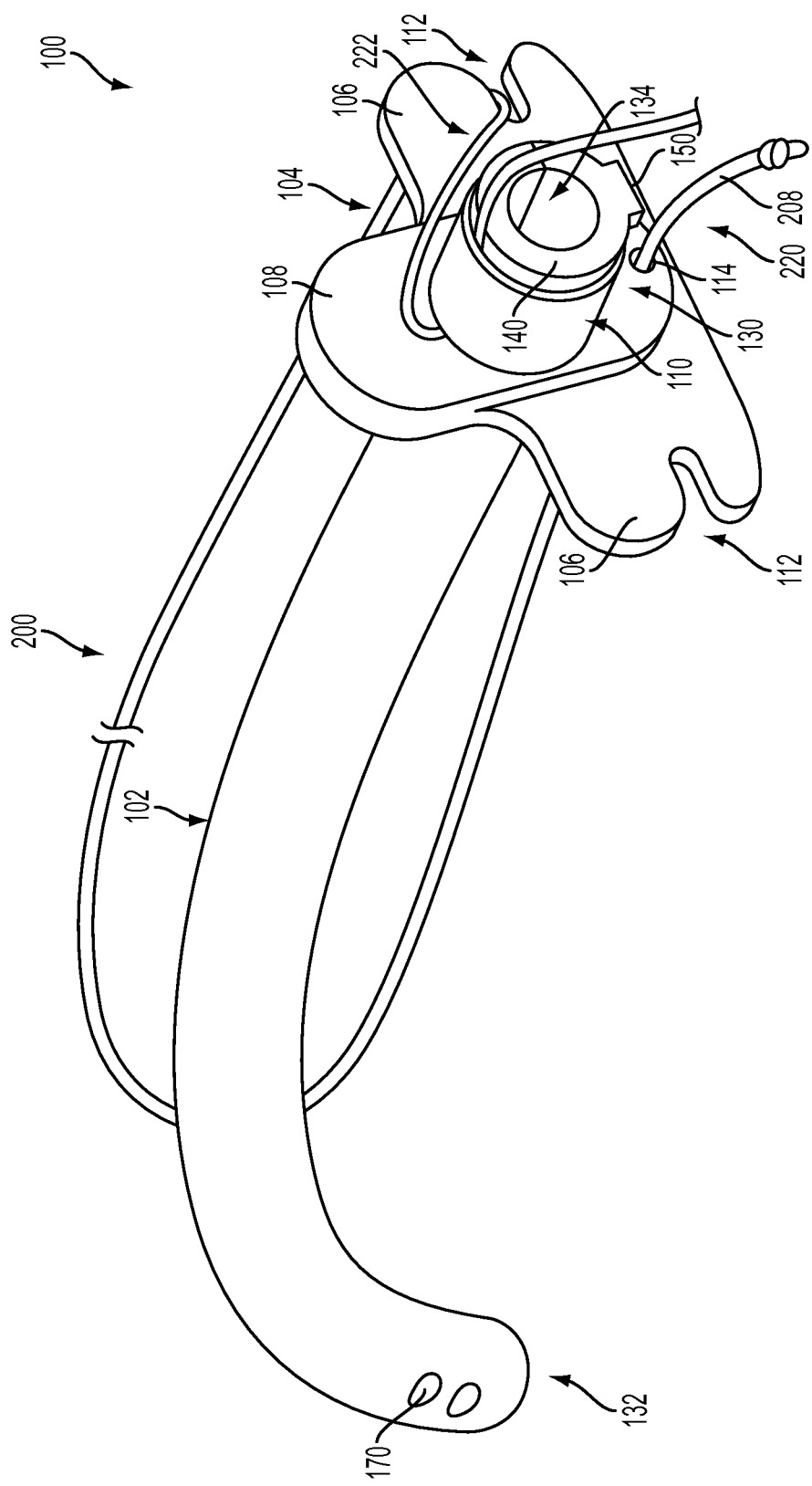
Figure 3:
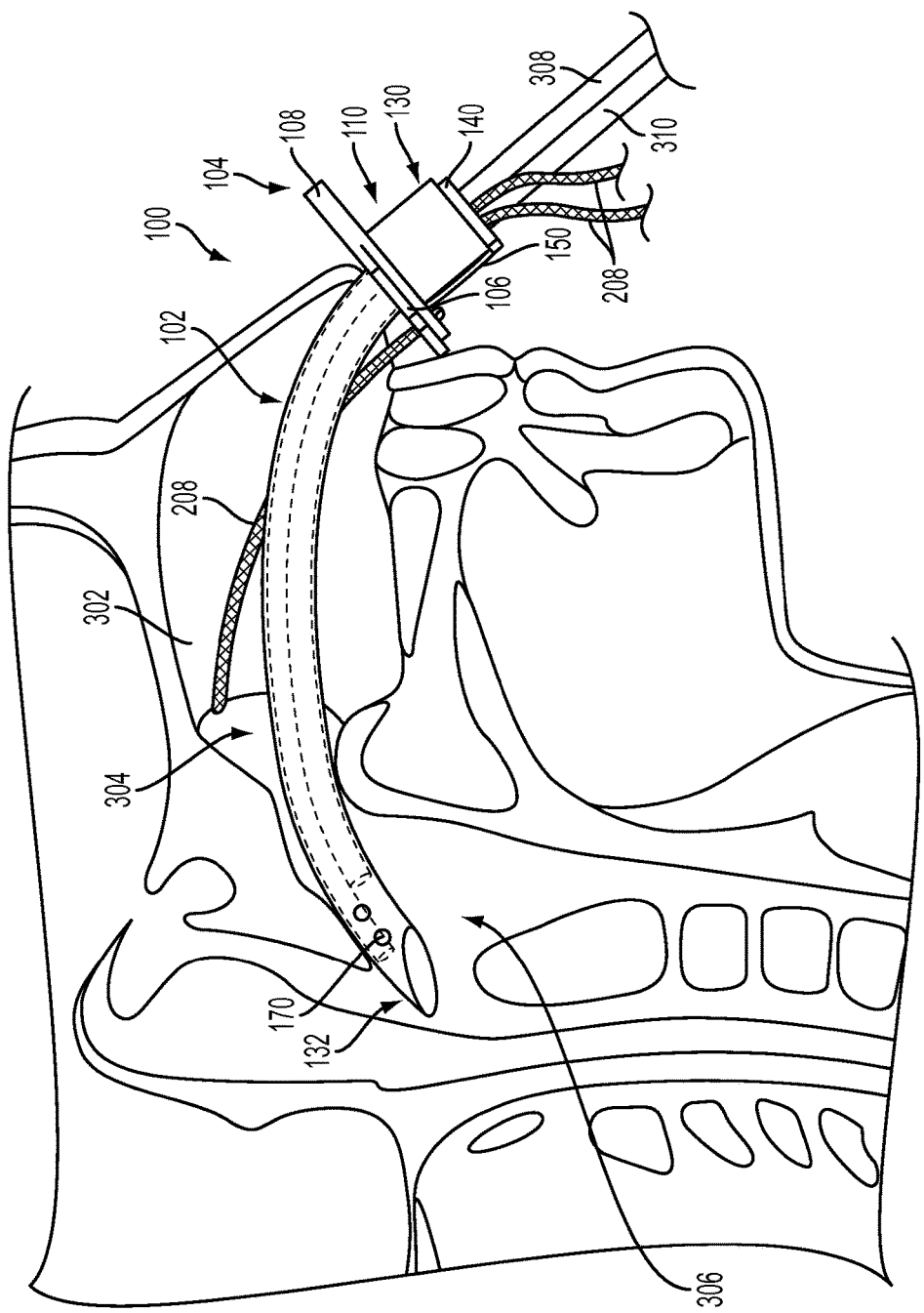
FIG. 3 is a partial cross sectional view of the nasal tube device of FIG. 1A, wherein the nasal tube device is positioned in a patient.

As illustrated in FIGS. 2A and 2B, the bridle line 208 is threaded through an opening 114 in the retention flange 104 and is knotted to prohibit removal of the line from the nasal tube device 100. In certain embodiments, the bridle line 208 may be attached near the proximal end 130 of the nasal tube 102 by threading the line through a hole in the nasal tube and knotting an end of the line to prohibit removal of the line from the nasal tube device 100. The bridle line 208 may also be tied such that a portion or tail of the line extends from the proximal end 130 of the nasal tube 102. However, the bridle line 208 may be attached to the nasal tube device 100 in a variety of other ways, such as, for example, with one or more ties, elastic bands, tape, glue or other adhesive, heat shrink tubing, clips or other fasteners or retainers. For example, the bridle line 208 may be attached to the nasal tube 102 with an adhesive and/or heat shrink tubing. Further, the bridle line 208 may be attached to one or more tubes extending from the lumen 134 of the nasal tube 102, such as, for example, oxygen and carbon dioxide tubes (e.g., with a clip, adhesive and/or heat shrink tubing). The bridle line 208 may also be overmolded with the nasal tube 102 to attach the line to the nasal tube device 100.

One exemplary method of placing and securing the nasal tube device 100 to a patient includes inserting the distal end of the catheter 202 into a first nostril of the patient and the distal end of the connecting member 260 into a second nostril of the patient. In a normal patient anatomy, the pathways of the two nostrils travel substantially parallel to one another until they terminate into the nasopharnyx 304 (see FIG. 3). The distal ends of the catheter 202 and the connecting member 260 are advanced into the nasopharnyx 304. The first connector 206 of the catheter 202 meets the second connector 262 of the connecting member 260 in the nasopharnyx 304 to establish a connection. In certain embodiments, the first and second connectors are magnets that attach together when placed in proximity to one another. Once connected, the connecting member 260 is retracted out of the second nostril. Retraction of the connecting member 260 pulls the catheter 202 and the bridle line 208 around the posterior free edge of the vomer 302 (FIG. 3) above the palate and bordering the anterior portion of the nasopharnyx 304. As the catheter 202 and the bridle line 208 are wrapped around the vomer 302, the nasal tube 102 is advanced into the first nostril of the patient and positioned such that the distal end 132 of the nasal tube terminates in a pharyngeal space of the patient, such as for example, the oropharyngeal or largyngopharyngeal space of the patient.

In certain embodiments, an elongated member, such as a flexible wire, is used with the catheter 202 to facilitate delivery and placement of the first connector 206 into the nasopharnyx 304 or pharyngeal space of the patient. Once a connection is established, the elongated member is removed from the catheter 202. In certain embodiments, the elongated member is inserted through an opening in the proximal end of the catheter 202. The elongated member may comprise a wire that extends into the catheter 202. The elongated member may also extend substantially the entire length of the catheter 202 and abut the first connector 206. The wire is generally more rigid than the catheter 202, yet flexible and resilient such that it may be bent to travel through the nostril and nasal passages of the patient and into the nasopharnyx. Further, in certain embodiments, the connecting member 260 may include bends or twists to facilitate connection of the second connector 262 with the first connector 206 of the catheter 202 in the nasopharnyx 304, such as by rotating the connecting member in the nose.

The nasal tube device 100 eliminates a step in the overall placement and securement procedure for the nasal tube. For example, when a separate nasal tube and nasal tube retention system is used, the bridle line of the retention system is first routed around the vomer 302 of the patient and then the nasal tube is placed over the bridle line. If adequate tension is not maintained on the bridle line during placement of the nasal tube, the line may become dislodged or pulled out of position. The nasal tube device 100 eliminates this step of placing the nasal tube over the bridle line. Further, the nasal tube device 100 of the present application permits the nasal tube 102 to be inserted with anesthesia lines, such as oxygen and carbon dioxide lines, already placed inside the lumen 134 of the nasal tube.

The bridle line 208 of the retention system 200 may be a variety of members that are flexible or semi rigid such that they may be wrapped around the vomer bone 302 and extend out a nostril of the patient. For example, in certain embodiments, the bridle line 208 may comprise one or more pieces of fabric (e.g., an umbilical tape or string), cord, or tubing. Further, the bridle line 208 may be fiber reinforced or elastomeric, and may be configured such that it does not excessively elongate to prohibit unwanted movement of the nasal tube 102 relative to the patient. It should also be noted that, in certain embodiments, the bridle line 208, the catheter 202, and/or the first connector 206 may be integrally formed as a unitary component of the retention system 200. For example, in one embodiment, the bridle line 208 and the catheter 202 may be formed as a single member that is flexible or semi rigid such that it may be wrapped around the vomer bone 302 and extend out a nostril of the patient.

FIG. 3 illustrates the nasal tube device 100 in position and secured to a patient with the bridle line 208 wrapped around the vomer 302. As shown, the distal end 132 of the nasal tube 102 terminates in the oropharyngeal space 306 of the patient. However, in certain embodiments, the distal end 132 of the nasal tube 102 may terminate in the largyngopharyngeal space of the patient or may extend into the esophagus of the patient and terminate in the alimentary tract to aid in nutrient delivery, drug delivery, endoscopy, decompression, etc. As shown in FIGS. 2B and 3, the bridle line 208 extends from the retention flange 104, through the first nostril, around the vomer 302, and out the second nostril of the patient. As discussed in greater detail below, the first and second portions of the bridle line 208 extending from the nostrils may be attached to the nasal tube device 100 using the retention flange 104 and/or the securing device 110. As illustrated in FIGS. 2B and 3, the securing device 110 is capable of receiving the bridle line 208 for securing the nasal tube device 100 to the patient.

The type and/or size of the nasal tube 102 may vary depending on a variety of factors, such as the medical purpose of the device and/or the size of the patient. As illustrated in FIGS. 1A-3, the nasal tube 102 is an NPA or nasal trumpet that facilitates the introduction of anesthesia lines or tools such as suction catheters or video equipment into the patient. The nasal tube 102 is configured for insertion through the patient's nose and nasal cavity to secure an open airway, such as when a patient experiences reduced levels of consciousness (e.g., during surgery) and airway muscle relaxation. As illustrated in FIG. 3, the nasal tube 102 is configured to be inserted into the nose and advanced to pass through the nasal pharynx with its distal end terminating above or below the base of the tongue depending upon the medical purpose. The nasal tube 102 is curved to conform to the anatomy of the nose and pharynx and aid in tube placement. The nasal tube 102 may also be circular or ovoid in cross-section to conform to the anatomy of the nasal passage. In certain embodiments, the nasal tube 102 may be constructed of a soft rubber polymer or silicone. A lubricant may also be applied to the surface of the nasal tube 102 to reduce friction during placement. In certain embodiments, the surface of the tube 102 may be treated with a lubricious coating or a coating which becomes lubricious in the presence of fluid to achieve reduced placement friction.

As illustrated in FIG. 3, the nasal tube device 100 comprises an oxygen delivery tube 308 and a carbon dioxide monitoring tube 310 inserted into the lumen 134 of the nasal tube 102. The nasal tube 102 comprises holes or openings 170 at or near its distal end 132 to aid in gas exchange and prevent tube occlusion. Further, the oxygen delivery tube 308 and the carbon dioxide monitoring tube 310 are positioned in the nasal tube 102 such that they terminate at different body levels relative to one another. Terminating the outlet of the oxygen delivery tube 308 and the inlet of the carbon dioxide monitoring tube 310 at different levels reduces the risk that the delivered oxygen will interfere with monitoring of returning carbon dioxide. As illustrated in FIG. 3, the outlet of the oxygen delivery tube 308 is positioned below the inlet of the carbon dioxide monitoring tube 310.

However, it is contemplated that the nasal tube device 100 may comprise oxygen delivery and carbon dioxide monitoring lumens or tubes configured in a variety of ways. For example, the inlet of the carbon dioxide monitoring lumen/tube may be positioned at a variety of locations relative to the outlet of the oxygen delivery lumen/tube. In various embodiments, the inlet of the carbon dioxide monitoring lumen/tube may be positioned above, below, or at approximately the same position as the outlet of the oxygen delivery lumen/tube. Further, the lumens or tubes may comprise a variety of terminations. For example, each of the lumens or tubes may terminate at one or a plurality of openings or regions in the nasal tube 102 (e.g., the side or end of the nasal tube). Further, the terminations of the lumens or tubes may comprise one or more features that prohibit clogging of the termination, such as a screen, filter, or porous region. For example, each of the lumens or tubes may terminate at one or more porous regions along the side or end of the nasal tube. Thus, the nasal tube device 100 is not limited to the outlet of the oxygen delivery tube 308 positioned below the inlet of the carbon dioxide monitoring tube 310.

As illustrated in FIG. 3, when the nasal tube device 100 has been properly positioned on the patient, the retention flange 104 is disposed adjacent the rim of the naris and external to the nasal passage of the patient. The retention flange 104 prohibits unwanted advancement of the nasal tube device 100, protects the external surface of the naris and columella, locates the bridle line 208 relative to the nasal tube device, and secures the bridle line to the device.

The retention flange 104 of the nasal tube device 100 may be a variety of shapes and sizes. For example, as illustrated in FIGS. 1A-3, the retention flange 104 is generally disposed perpendicular to the length of the nasal tube 102. A central portion 108 of the retention flange 104 projects above the nasal tube 102 and rests substantially parallel to the columella when the device 100 is properly positioned on the patient. The retention flange 104 also comprises right and left tab portions 106 which extend substantially perpendicular from the central portion 108. The tab portions 106 and the central portion 108 of the retention flange 104 facilitate proper placement of the nasal tube device 100 and prohibit unwanted advancement of the device. Further, the bottom of the retention flange 104 is generally straight to accommodate the upper lip and philtrum of the patient.

The retention flange 104 may comprise one or more features for locating and/or securing the bridle line 208. For example, as illustrated in FIG. 2B, the tab portions 106 of the retention flange 104 comprise one or more notches 112 that may be used to accept and locate the bridle line 208. As shown, the second portion 222 or the portion of the bridle line 208 extending from the second nostril may pass through the notch 112 and extend over the external surface of the retention flange 104 to the securing device 110. As such, the tab portions 106 permit tensioning of the bridle line 208, and the notches 112 hold and locate the tensioned bridle line without the bridle line directly contacting the columella. Thus, the tab portions 106 protect the columella from the tensioned bridle line 208. In certain embodiments, the tab portions 106 may be thinner than the central portion 108 of the retention flange 104 to conform to the anatomy of the columella. The tab portions 106 of the retention flange 104 also permit use of the nasal tube device 100 in either the left or the right nostril, e.g., the device may comprise right and left tab portions that are identical or substantially similar. Further, as illustrated in FIGS. 2A and 2B, the portion of the retention flange 104 below the nasal tube 102 comprises the opening 114 for attaching the retention system 200 to the nasal tube device 100. As shown, the bridle line 208 is threaded through the opening 114 and is knotted to prohibit removal of the line from the nasal tube device 100.

The retention flange 104 may be attached to or integrally formed with the nasal tube 102. In certain embodiments, the retention flange 104 is movable relative to the nasal tube 102. For example, the retention flange 104 may be adjusted relative to the nasal tube 102 to adjust the insertion length of the nasal tube depending on the size of the patient and/or the medical need of the nasal tube device 100.

As illustrated in FIGS. 1A-3, the proximal end 130 of the nasal tube 102 comprises a lip or flange 140 forming a nest region or recessed portion 142 between the retention flange 104 and the proximal end of the nasal tube. As shown, the securing device 110 is disposed in the recessed portion 142 and is configured to selectively compress the nasal tube 102. As illustrated in FIGS. 1A-4, the securing device 110 is a hinged clip that substantially surrounds the external surface of the recessed portion 142 of the nasal tube 102 and compresses the nasal tube in the closed position. However, a variety of other securing devices may be used that selectively compress the nasal tube 102, such as, for example, other clips, various fasteners, clamps, elastic bands or tubing, retainers, spring devices, or the like.

The nasal tube device 100 may comprise one or more retaining features for attaching the securing device 110 to the nasal tube 102. As such, the securing device 110 is integrated with the nasal tube 102, which reduces the risk associated with accidental oral aspiration or ingestion of a separate bridle clip that generally sits above the upper lip. For example, as illustrated in FIGS. 1A-3, the retaining feature is in the form of a retaining strap 150 extending from the proximal end 130 of the nasal tube 102 to the retention flange 104. However, the securing device 110 may be attached to the nasal tube 102 in a variety of other ways, such as, for example, with one or more fasteners, ties, elastic bands, adhesive, heat shrink tubing, clips, clamps, or other fasteners or retainers.

In certain embodiments, the retention flange 104 and/or nasal tube 102 may comprise retaining features for attachment and integration of the securing device 110. For example, the portions of the retention flange 104 adjacent the securing device 110 (e.g., the central portion 108) and/or the portions of the nasal tube 102 adjacent the securing device (e.g., the flange 140) may comprise one or more retaining features, such as, for example, a lip, edge, groove, channel, or the like, configured to attach the securing device to the nasal tube. In one embodiment, the central portion 108 and the flange 140 comprise a circular undercut portion that at least partially surrounds the recessed portion 142 of the nasal tube 102 and forms a lip or flange that retains the securing device 110.

The retaining strap 150 may be attached to or integrally formed with the nasal tube 102 and/or the retention flange 104. As illustrated in FIGS. 1A-3, the securing device 110 is received or disposed in a space formed between the retaining strap 150 and the recessed portion 142 of the nasal tube 102. As such, the retaining strap holds the securing device relative to the nasal tube and attaches the securing device to the nasal tube device. Further, as illustrated in FIGS. 1A and 1B, the securing device 110 is secured to the nasal tube 102 in both the open and closed positions to prohibit loss of the securing device. As shown, the securing device 110 is also held between the retention flange 104 and the flange 140 of the nasal tube 102.

The nasal tube 102 may be separated or split in one or more sections (e.g., a discontinuous wall) to facilitate selective placement, adjustment and/or securement of one or more additional medical tubes, wires or medical instruments which may pass into the lumen 134 of the nasal tube. For example, as illustrated in FIG. 1A, the recessed portion 142 of the nasal tube 102 is separated when the securing device 110 is in the open position. The separation 160 extends from the retention flange 104 to the proximal end 130 of the nasal tube 102. As illustrated in FIG. 1B, when the securing device 110 is closed, the recessed portion 142 of the nasal tube 102 is compressed and the inner diameter of the lumen 134 is reduced to hold the medical tubes, wires or medical instruments within the lumen. As shown, the edges of the separated portion 160 are compressed closer together as the securing device is closed. As such, the securing device 110 encloses the recessed portion 142 and provides controlled compression of the recessed portion against the medical tubes, wires, or instruments passing into the lumen 134 of the nasal tube 102. The applied friction of the inner surface of the lumen 134 against the medical tubes, wires, or instruments selectively secures them to the nasal tube 102. The securing device 110 also simplifies placement and operation of the nasal tube device 100 for the user and may be used to retain the medical tubes, wires, or instruments without coupling the same directly to a bridle system.

Figure 4:
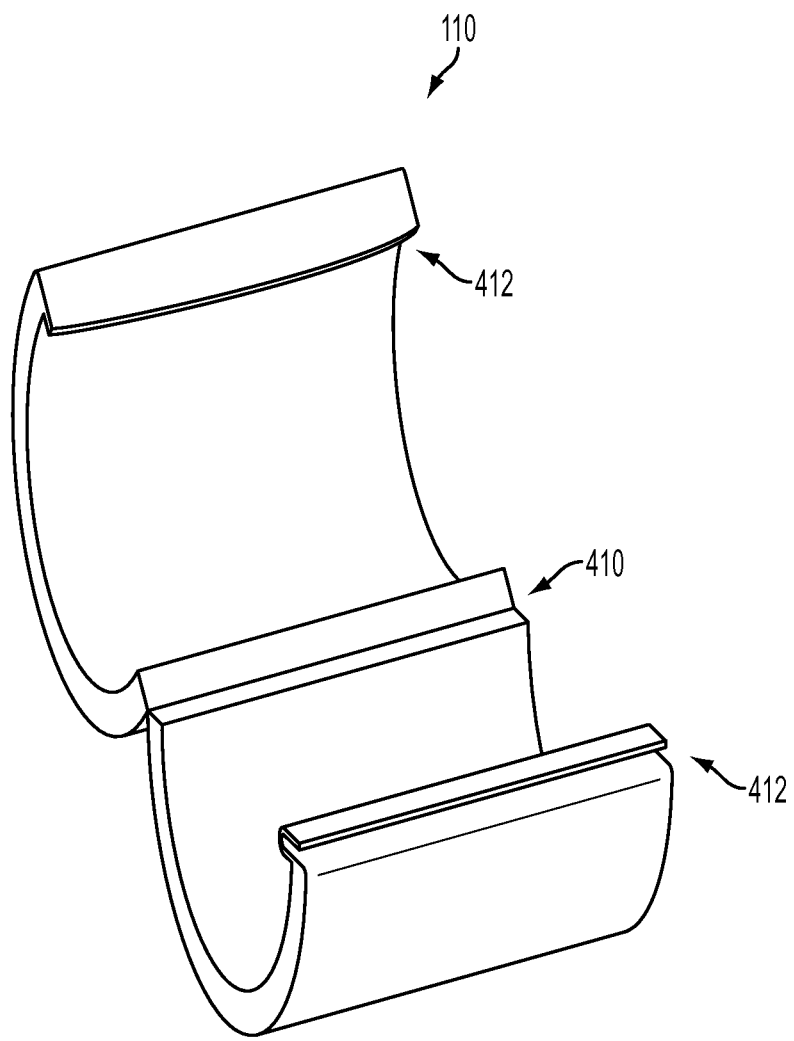
FIG. 4 is a perspective view of a securing device according to an embodiment of the present application.

FIG. 4 illustrates the securing device 110 in an open position and removed from the nasal tube 102. As shown, the securing device 110 is a clip having a hinge 410 (e.g., a living hinge) to allow the body of the clip to pivot between open (unlocked) and closed (locked) positions. The clip also comprises a tongue-and-groove style locking mechanism 412 which permits the clip to repeatedly open and close during its use. The clip may be constructed of a variety of materials. For example, in certain embodiments, the clip is constructed of a rigid molded polymer material such as polypropylene. Further, the shape of the clip when locked generally approximates the external shape of the recessed portion 142 of the nasal tube 102. The clip may also have surface textures, depressions, projections, and/or curvatures on its external surface to facilitate its operation.

As illustrated in FIG. 2B, the bridle line 208 may be placed between the securing device 110 and the nasal tube 102 to secure the nasal tube device 100 to the patient. As shown, the bridle line 208 extends from the opening 114 in the retention flange 104. Although not shown in FIG. 2B, the bridle line 208 may then extend through the first nostril, around the vomer 302 (FIG. 3), and out the second nostril of the patient. The second portion 222 of the bridle line 208 extending from the second nostril passes through one or more notches 112 of the tab portions 106 and extends over the external surface of the retention flange 104 to the securing device 110. The second portion 222 of the bridle line 208 is then routed between the securing device 110 and the recessed portion 142 of the nasal tube 102 such that the bridle line is secured to the nasal tube when the securing device is closed. Further, as illustrated in FIG. 2B, the first portion 220 of the bridle line 208 is knotted to aid securement of the bridle system 200 to the nasal tube device 100. However, in certain embodiments, a first portion 220 of the bridle line 208 may also be secured to the nasal tube 102 with the securing device 110 by any of the methods described herein. For example, the first portion 220 of the bridle line 208 may be routed between the securing device 110 and the recessed portion 142 of the nasal tube 102 such that the first portion of the bridle line is also secured to the nasal tube when the securing device is closed.

Figure 2C:
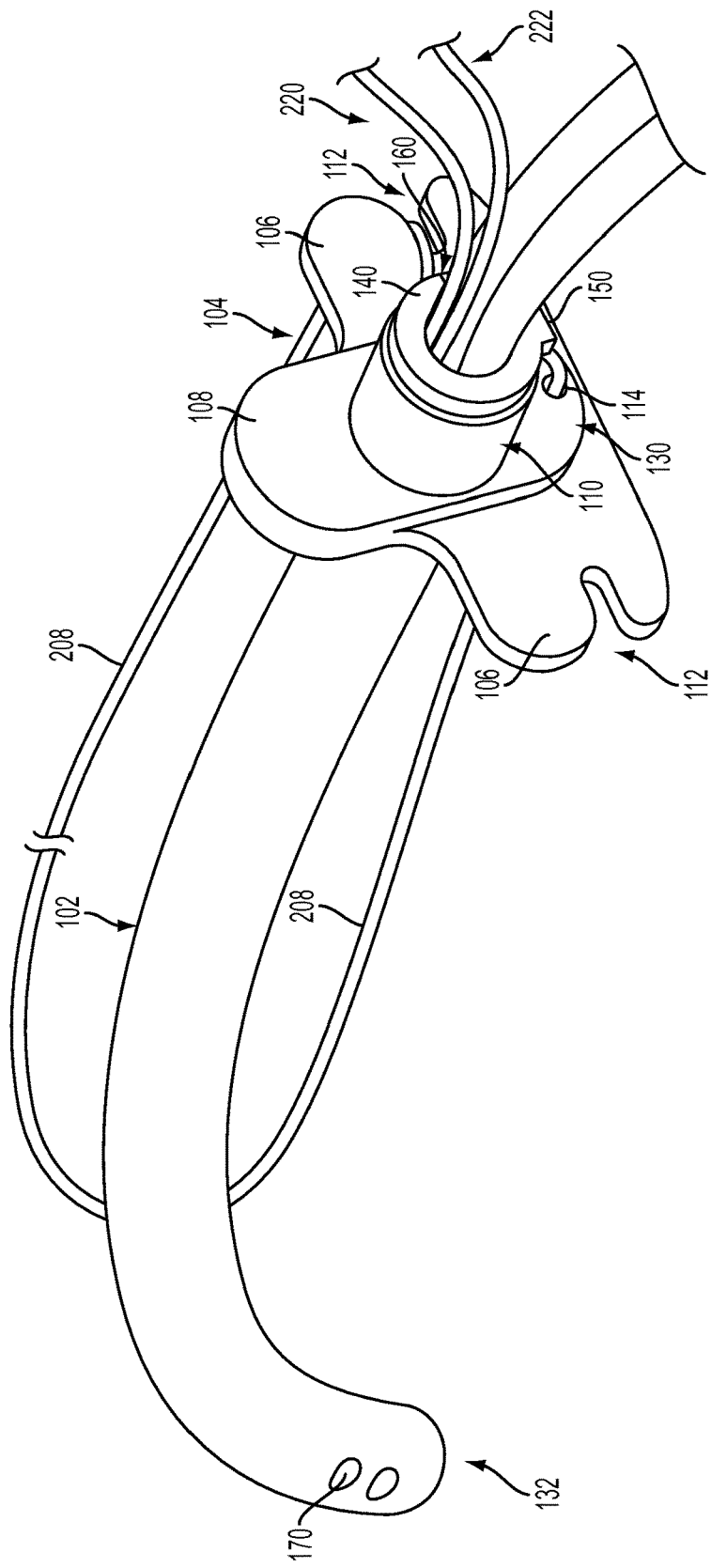

The bridle line 208 may also be routed through the separated portion 160 of the nasal tube 102 and/or between medical tubes, wires, or medical instruments passing into the lumen 134 of the nasal tube such that the bridle line is secured to the nasal tube when the securing device 110 is closed. For example, as illustrated in FIGS. 2C and 3, the bridle line 208 extends from the opening 114 in the retention flange 104, through the first nostril, around the vomer 302, and out the second nostril of the patient. The second portion 222 of the bridle line 208 extending from the second nostril then passes through one or more notches 112 of the tab portions 106 and extends over the external surface of the retention flange 104 to the securing device 110. The second portion 222 of the bridle line 208 is routed beneath the securing device 110, through the separated portion 160 of the nasal tube 102, and out the lumen 134 such that the bridle line is secured to the nasal tube when the securing device 110 is closed. As shown, medical tubes also extend out the lumen 134 of the nasal tube 102 and are secured to the nasal tube when the securing device 110 is closed. Further, as illustrated in FIG. 2C, the first portion 220 of the bridle line 208 is also routed beneath the securing device 110, through the separated portion 160 of the nasal tube 102, and out the lumen 134 such that the first portion is secured to the nasal tube when the securing device 110 is closed. However, the first portion 220 of the bridle line 208 may be secured to the nasal tube 102 by any of the methods described herein. Further, the first and second portions 220 and 222 extending out of the lumen 134 may also be knotted and/or wrapped around the nasal tube 102 and/or the medical tubes to further secure the bridle line 208 to the nasal tube device 100.

The nasal tube device 100 may be used for a number of medical purposes. For example, in certain embodiments, the nasal tube device 100 may be used as an oxygen delivery and/or carbon dioxide monitoring aid to support anesthesiology activities. For example, as illustrated in FIG. 3, an oxygen delivery tube and/or a carbon dioxide sampling tube may pass through the main lumen 134 of the nasal tube device 100 and be secured to the device using the securing device 110. The oxygen tube and the carbon dioxide tube may also be adjusted relative to one another to optimize oxygen delivery and carbon dioxide sampling by use of the securing device 110 and its ability to open and lock repeatedly. In certain embodiments, one or more oxygen delivery tubes securely interface with the nasal tube device 100 using the mechanisms described above. Yet another medical purpose of the nasal tube device 100 may be to securely protect a patent airway in a similar fashion to a traditional nasopharyngeal airway device. The nasal tube device 100 has a number of advantages over traditional nasopharyngeal airways, notably including the ability to accept a nasal bridle system so as to secure the nasal tube device in position. The integrated securing device 110 further allows medical tubes, wires, or instruments to securely interface with the nasal tube device, for all or just part of the device's useful life in the patient. The nasal tube device 100 of the present application also couples the benefits of bridle system securement with the temporary use of one or more medical tubes, wires, or medical instruments without directly interfacing or disturbing that bridle securement.

Figure 5A:
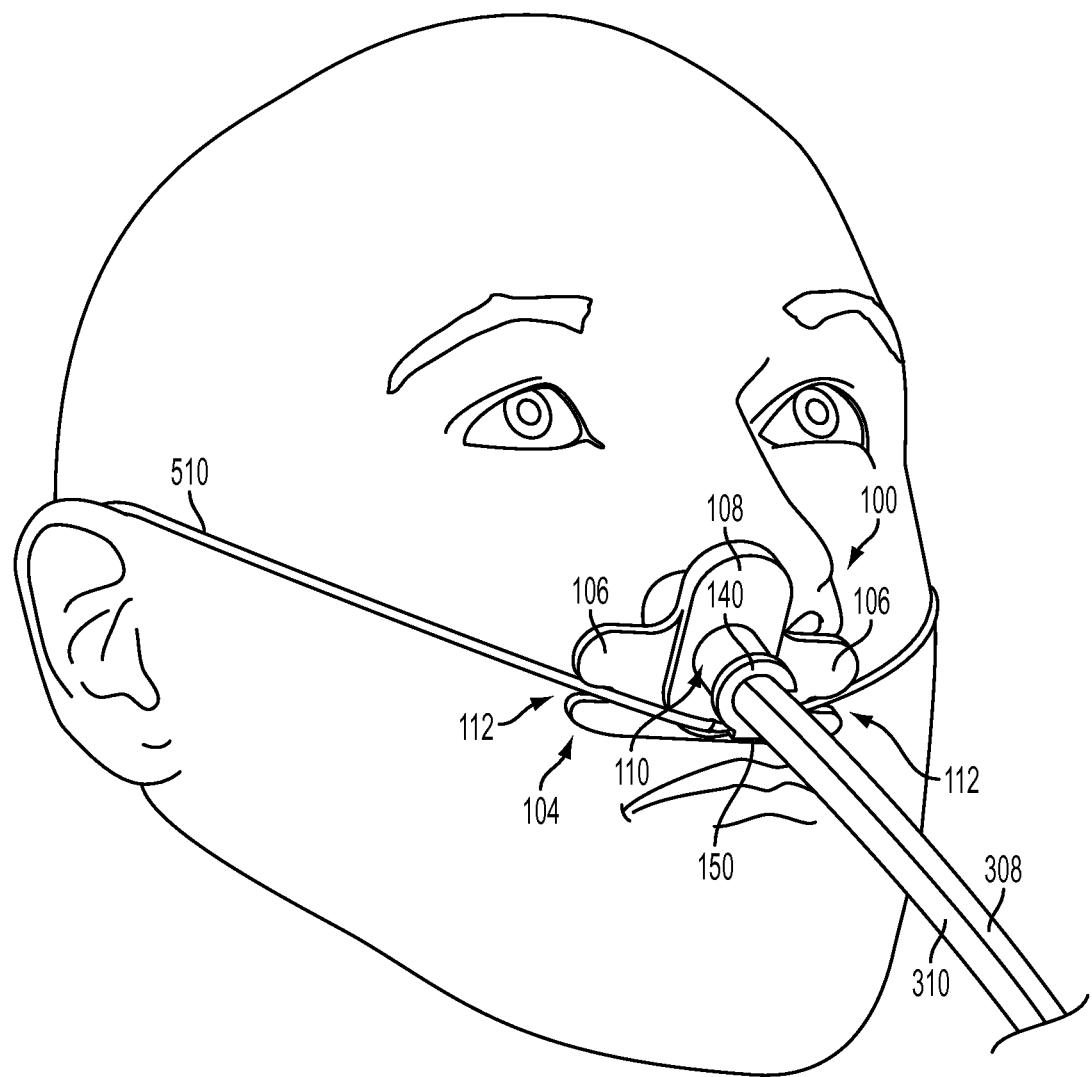
FIG. 5A is a perspective view of the nasal tube device of FIG. 1A secured to a patient with a retention system according to an embodiment of the present application.
Figure 5B:
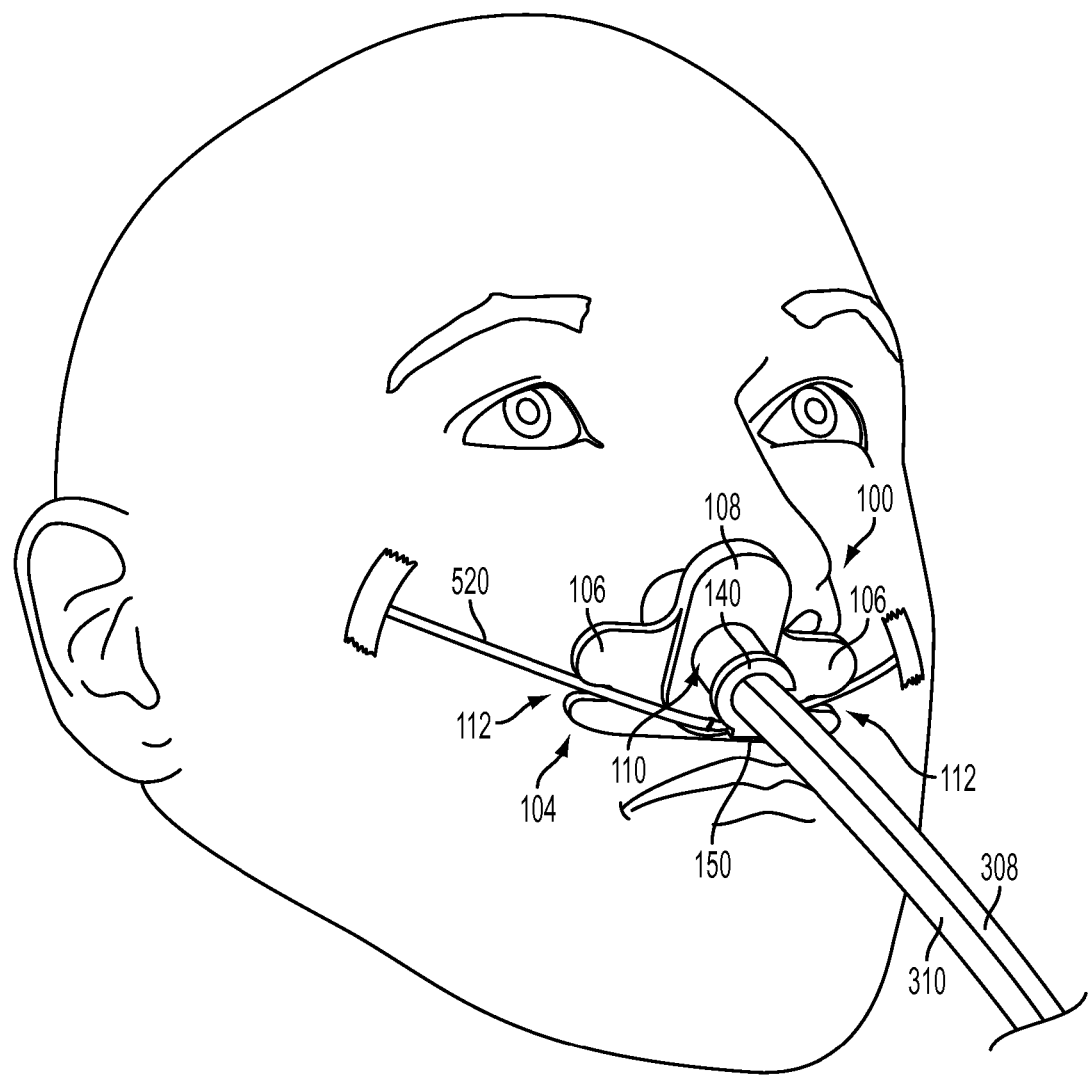
FIG. 5B is a perspective view of the nasal tube device of FIG. 1A secured to a patient with a retention system according to an embodiment of the present application.

The retention flange 104 of the nasal tube device may be used in a variety of ways to hold the nasal tube device 100 in position and secured to the patient. For example, FIGS. 5A and 5B illustrate alternative ways of securing the nasal tube device 100 to a patient without passing a bridle line through the nostrils and around the vomer bone 302 of the patient. As illustrated in FIG. 5A, a bridle line 510 extends from one or more openings in the retention flange 104, passes through the notches 112 of the tab portions 106, and extends around the head of the patient to hold the nasal device 100 in place and secured to the patient. Similarly, as illustrated in the FIG. 5B, a bridle line 520 extends from one or more openings in the retention flange 104, passes through the notches 112 of the tab portions 106, and the ends of the bridle line are taped to the head of the patient to hold the nasal device 100 in place and secured to the patient.

The nasal tube device of the present application may comprise a nasal tube that is configured to deliver at least a portion of the nasal tube retention system into the appropriate pharyngeal space to secure the nasal tube to the patient. For example, a connector of the retention system may be delivered via a lumen or passage of the nasal tube. As such, the nasal tube device increases the ease of delivery of the retention system for the health care provider. The delivery of a connector contained in a nasal tube reduces the procedural delicacy and dexterity required to deliver a traditional nasal retention system. Further, delivery of the connector via a lumen or passage of the nasal tube facilitates proper orientation of the connector and prohibits unwanted movement of the connector. For example, when magnets are used, control and proper orientation of the magnet is desirable to establish a magnetic connection between the first and second magnetic connectors. A magnetic connection may fail to occur if the first and second magnets present the same polar magnetic field during placement.

FIGS. 6A-8 illustrate a nasal tube device 600 according to an embodiment of the present application. The nasal tube device 600 comprises a nasal tube 602 having a proximal end 630 and a distal end 632, a retention flange 604, and a securing device 610. As shown, the nasal tube 602 comprises a main lumen 634 extending from the proximal end 630 to the distal end 632 of the nasal tube.

Figure 6A:
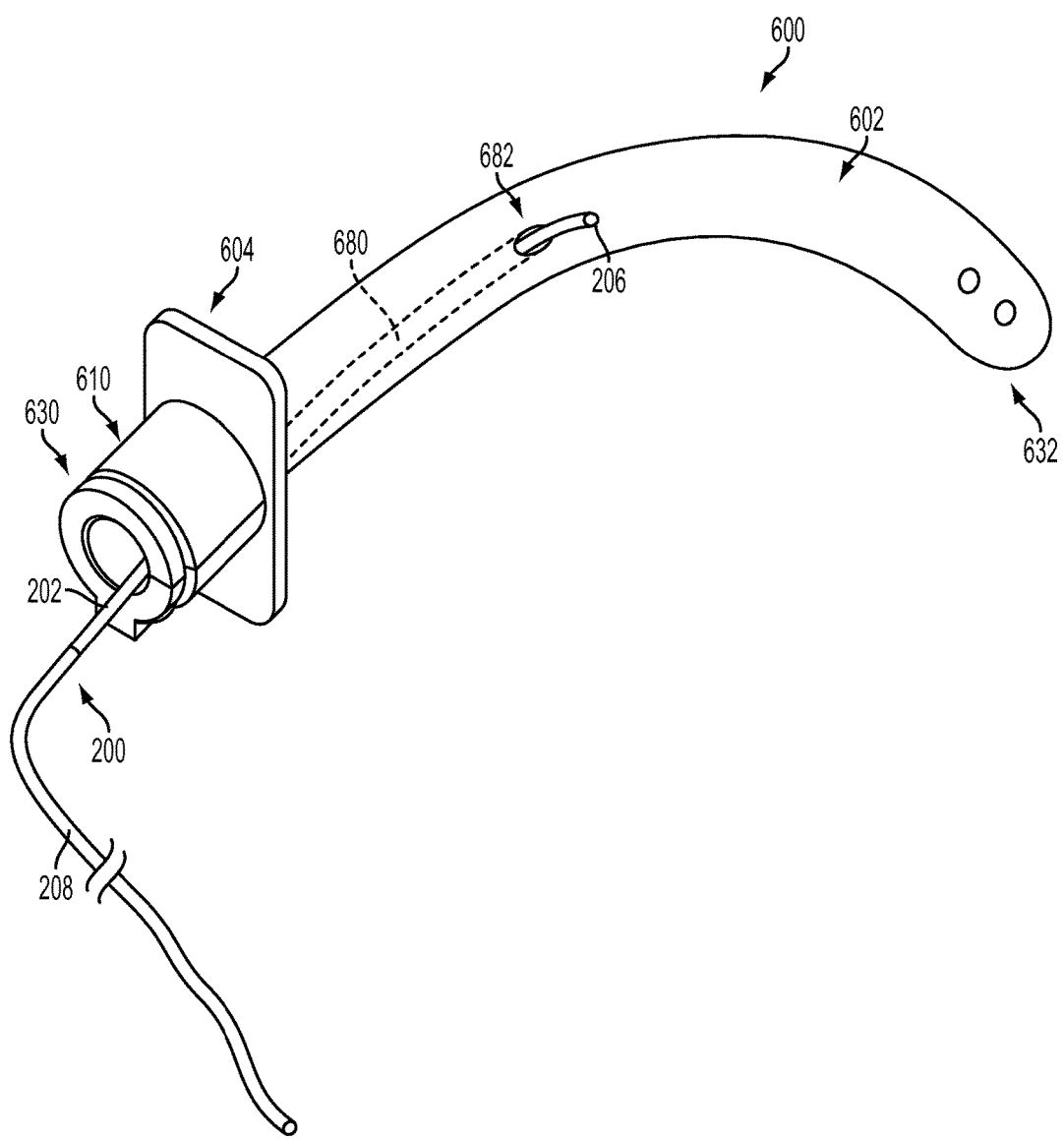
FIGS. 6A and 6B are perspective and side views, respectively, of a nasal tube device according to an embodiment of the present application, wherein the nasal tube device is attached to a retention system according to an embodiment of the present application.
Figure 6B:
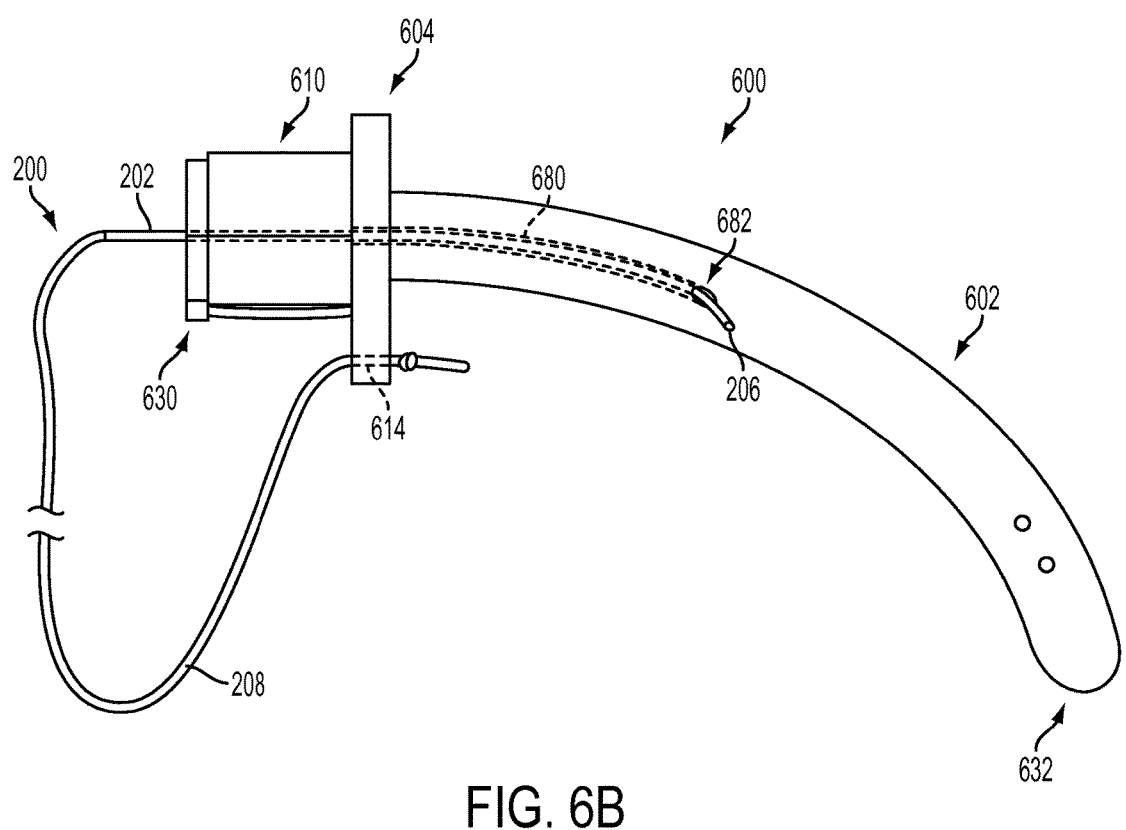

FIGS. 6A-6B illustrate the nasal tube device 600 attached to the exemplary retention system 200. The retention system 200 comprises the bridle line 208, catheter 202 having the first connector 206 at the distal end, and the connecting member (not shown) having the second connector at the distal end. The bridle line 208 is attached to the catheter 202 and the nasal tube device 600. As illustrated in FIG. 6B, the bridle line 208 is threaded through an opening 614 in the retention flange 604 and is knotted to prohibit removal of the line from the nasal tube device 600. The first and second connectors may be a variety of devices or fasteners configured to connect or otherwise attach together, e.g., when touched together or when placed in close proximity to one another. For example, in certain embodiments, the first and second connectors are magnets that attach together when placed in proximity to one another.

Figure 7:
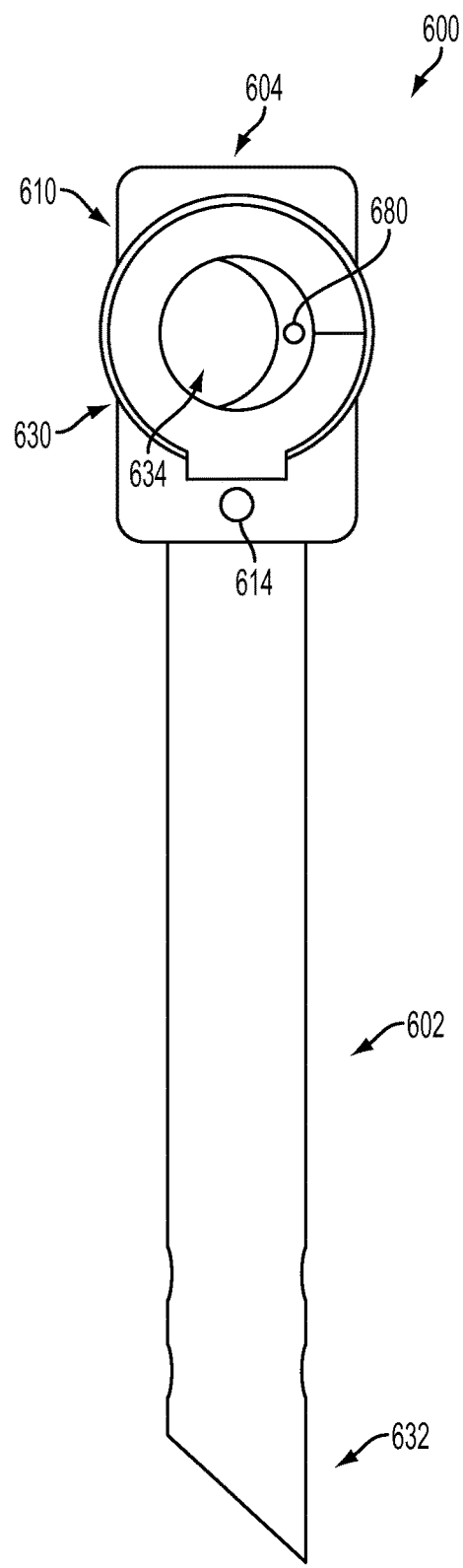
FIG. 7 is a front view of the nasal tube device of FIGS. 6A and 6B.
Figure 8:
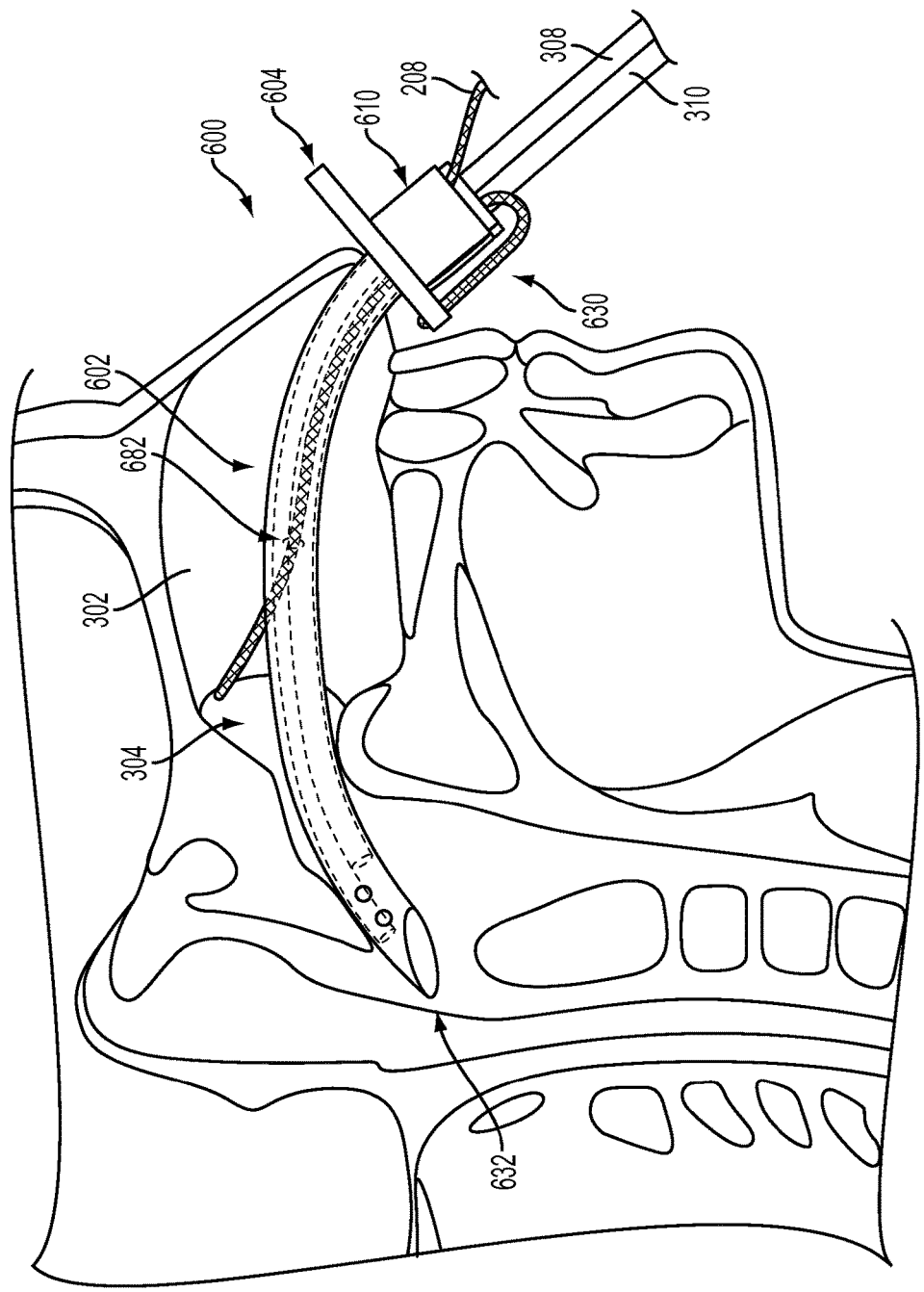
FIG. 8 is a partial cross sectional view of the nasal tube device of FIGS. 6A and 6B, wherein the nasal tube device is positioned in a patient.

The nasal tube device 600 is configured to deliver the connector 206 of the retention system 200 via a lumen or passage of the nasal tube 602. As illustrated in FIGS. 6A-8, the nasal tube 602 comprises a delivery lumen 680 extending from the main lumen 634 and terminating at a delivery window 682 or opening in the outer wall of the nasal tube. As illustrated in FIG. 7, the entrance opening to the delivery lumen 680 is located in the interior of the proximal portion of the nasal tube approximately at the retention flange 604.

As shown in FIGS. 6A-6B, the delivery window 682 is an opening in the outer wall of the nasal tube 602. In other embodiments, the connector 206 of the retention system 200 may be delivered through a delivery tube or passage formed on, extending from, or otherwise attached to the outer surface of the nasal tube 602.

As illustrated in FIGS. 6A-8, the entrance opening to the delivery lumen 680 is located inside the main lumen 634 of the nasal tube device 600. As such, the main lumen 634 and the delivery lumen 680 collectively form a delivery lumen or passage for the connector 206 of the retention system 200 extending from the proximal portion of the nasal tube to the delivery window 682. However, in certain embodiments, the delivery lumen 680 is completely separate from the main lumen 634, and the entrance opening for the delivery lumen is not located inside the main lumen. For example, the entrance opening may be located at the proximal end of the nasal tube, along with the entrance to the main lumen (or other lumens).

The delivery lumen 680 is configured to permit the bridle line 208 and/or the catheter 202 having the first connector 206 disposed at its distal end to travel through the delivery lumen and out the delivery window 682. As such, the nasal tube device 600 delivers the first connector 206 to the appropriate pharyngeal space for connection to the second connector of the connecting member of the retention system 200. In certain embodiments, the first and second connectors are magnets that attach together when placed in proximity to one another. Further, in certain embodiments, the delivery lumen 680 comprises a gentle curve exiting at the delivery window 682 to facilitate delivery of the first connector 206 to the appropriate pharyngeal space for connection to the second connector of the connecting member of the retention system 200. Further still, the end of the delivery lumen 680 terminating at the delivery window 682 may be tapered to facilitate delivery of the first connector 206 into the appropriate pharyngeal space of the patient.

It should be understood that the distance of the delivery window 682 from the proximal end 630 of the nasal tube 602 and the orientation of the delivery window on the circumference of the nasal tube will vary depending on the desired delivery location for the first connector 206.

For example, in certain embodiments, the nasal tube device 600 is configured such that the delivery window 682 delivers the first connector 206 into the nasopharnyx 304 (see FIG. 8) of the patient when the nasal tube 602 is in position. As such, the first connector 206 is positioned for connection to the connecting member of the retention system 200 that is inserted through the nostril of the patient and advanced into the nasopharnyx 304. In these embodiments, for an average adult, the delivery window 682 is generally between about 5 and 10 cm from the proximal end 630 of the nasal tube 602 along the longitudinal axis of the nasal tube. However, the location of the delivery window 682 will vary depending on the size of the patient and nasal tube 602, and in the cases of animals, the type of patient. For example, this distance may be significantly smaller for pediatric nasal tubes. Further, the delivery window 682 is generally orientated medially (i.e., facing the midline of the body) such that the first connector 206 will be positioned in close proximity to the connecting member. Further still, the delivery window 682 may be orientated such that the first connector 206 crosses the midline of the body on an intersecting trajectory with the connecting member.

In another embodiment, the nasal tube device 600 is configured such that the delivery window 682 delivers the first connector 206 into the oropharyngeal space of the patient when the nasal tube 602 is in position. As such, the first connector 206 is positioned for connection to the connecting member of the retention system 200 that is inserted through the mouth of the patient and advanced into the oropharyngeal space. The bridle line 208 is pulled through the mouth to establish retention of the nasal tube 602 both nasally and orally.

In this embodiment, the delivery window 682 may be between about 8 and 18 cm from the proximal end 630 of the nasal tube 602 along the longitudinal axis of the nasal tube. This distance will vary depending on the size of the patient and nasal tube 602. Further, depending on the embodiment, the delivery window 682 may be located at a variety of positions between the vomer 302 (FIG. 8) and the distal end 632 of the nasal tube 602. For example, in one embodiment, the delivery window 682 is located in the nasopharynx 304 and the catheter 202 is of sufficient length such that the first connector 206 may be delivered to the oropharyngeal space. The connecting member may then be inserted through the mouth of the patient to connect with the first connector 206 of the catheter 202. In another embodiment, the delivery window 682 is located more towards the distal end 632 of the nasal tube 602 such that the first connector 206 is delivered directly into the oropharyngeal space. Further, the orientation of the delivery window 682 is generally medial or inferior depending on the location of the delivery window along the length of the nasal tube 602.

An exemplary method of placing and securing a nasal tube to a patient using a nasal tube device having a nasal tube that is configured to deliver a connector of the retention system into the appropriate pharyngeal space is described below with reference to the nasal tube device 600 illustrated in FIGS. 6A-8. Further, the method is described with reference to the first connector 206 comprising a magnet such that the magnet is delivered into the appropriate pharyngeal space.

The method comprises advancing the nasal tube 602 of the nasal tube device 600 into a first nostril of the patient and positioning the nasal tube such that the distal end 632 terminates in a pharyngeal space of the patient, such as for example, the oropharyngeal or largyngopharyngeal space of the patient. The nasal tube 602 may or may not be inserted with anesthesia lines, such as oxygen and carbon dioxide lines, already placed inside the lumen 634 of the nasal tube. Anesthesia lines may also be placed into the nasal tube 602 one at a time to free a lumen for other uses. The bridle line 208 and/or catheter 202 of the retention system 200 is inserted into the delivery lumen 680 of the nasal tube 602 until the magnet 206 is deployed out the delivery window 682 and into the nasopharnyx 304 (see FIG. 8). An elongated member or pneumatic actuation may be used to facilitate deployment of the magnet 206 out the delivery window 682.

Once the magnet 206 is deployed, a magnetic connecting member of the retention system 200 is inserted into the second nostril of the patient and advanced into the nasopharnyx 304 to establish a connection with the magnet 206. It should be noted that it may be clinically advantageous to advance the delivery window 682 slightly beyond the targeted space, then retract the nasal tube 602 and/or twist the nasal tube to establish the magnetic connection with the connecting member. Further, the connecting member may have a slight bend to facilitate finding its magnetic opposite in the nasopharyngeal space by rotating the connecting member in the nose. Once the magnet 206 is connected to the magnetic connecting member, the connecting member is retracted out of the second nostril. Retraction of the connecting member pulls the bridle line 208 through the delivery lumen 680, around the posterior free edge of the vomer bone 302 (FIG. 8), and out the second nostril.

As described above with reference to the nasal tube device 100, the securing device 610 may be used in a variety of ways to secure the portions of the bridle line 208 extending from the nostrils to the nasal tube 602. As such, the vomer 302 anchors the nasal tube 602 against unwanted pullout or retreat and the columella of the nose anchors the nasal tube against unwanted advancement. Further, in certain embodiments, the portions of the bridle line 208 may be tied together or attached in a variety of ways, such as for example, with one or more ties, elastic bands, tape, adhesive, heat shrink tubing, clips or other fasteners or retainers. The portions of the bridle line 208 may also be attached or otherwise secured to the nasal tube 602 or components attached to the nasal tube, such as for example, anesthesia lines connected to the nasal tube.

As shown in FIGS. 6A and 6B, a flexible linear catheter or probe 202 is used to route the magnet 206 through the magnet delivery lumen 680 and out the magnet delivery window 682 of the nasal tube 602. However, a variety of other methods or devices may be used to deliver the magnet of the retention system into the appropriate pharyngeal space of the patient. For example, a curved catheter or probe may be used to route the magnet through the delivery lumen and out the delivery window. Further, a separate non-magnetic probe may be used to move the magnet through the delivery lumen and out the delivery window. For example, in certain embodiments, the magnet is attached directly to the flexible bridle line of the retention system and the separate probe is used to move the magnet. It should be noted that, in certain embodiments, an additional member, such as a probe or elongated member, is not required to deliver the magnet of the retention system through the magnet delivery lumen and out the magnet delivery window of the nasal tube. Instead, the nasal tube may be configured such that the magnet may be routed through the delivery lumen and out the delivery window without use of another device or member.

In certain embodiments, the magnet delivery lumen is configured such that a magnet of the retention system is delivered to the appropriate pharyngeal space of the patient by pulling the line through the delivery lumen. More specifically, the magnet delivery lumen comprises an entrance window and an exit window in the side of the nasal tube. The line is threaded through the magnet delivery lumen, out the exit window, into the entrance window, and back up through the delivery lumen to the proximal end of the nasal tube. Pulling the line through the magnet delivery lumen positions the magnet (which is attached to the flexible line) between the entrance and exit windows such that it is exposed. A magnetic connecting member may then be used to establish a connection with the exposed magnet.

The nasal tube device of the present application may be configured to be used as a dedicated anesthesiology monitoring/oxygen delivery device. For example, in certain embodiments, the nasal tube device comprises a molded polymer nasal tube having three lumens or passages. A magnet delivery lumen extends from a proximal end of the nasal tube to a magnet delivery window on the side of the nasal tube. The magnet delivery lumen is used to deliver a magnet of the retention system into the appropriate pharyngeal space of the patient. An oxygen delivery lumen extends from the proximal end of the nasal tube to an opening at the distal end of the nasal tube. The oxygen delivery lumen is configured to deliver oxygen to the patient. A carbon dioxide monitoring lumen extends from the proximal end of the nasal tube to an opening in the side of the nasal tube towards the distal end of the nasal tube. The carbon dioxide monitoring lumen facilitates the passage of expired air from the patient to a carbon dioxide monitoring device. The nasal tube may be configured such that the oxygen delivery and carbon dioxide monitoring lumens terminate at different levels relative to one another. With the oxygen delivery outlet positioned below the inlet of the carbon dioxide monitoring lumen, the delivered oxygen does not interfere with monitoring of returning carbon dioxide.

Furthermore, in other embodiments, the nasal tube device comprises a molded polymer nasal tube having a magnet delivery lumen. Further, an oxygen delivery tube and a carbon dioxide monitoring tube are overmolded with the nasal tube to faun the nasal tube device. The proximal ends of the oxygen delivery tube and the carbon dioxide monitoring tube comprise connectors for attachment to the corresponding oxygen delivery and carbon dioxide monitoring device(s). The oxygen delivery tube forms an oxygen delivery lumen of the nasal tube that extends from the proximal end of the nasal tube to an opening at the distal end of the nasal tube. The carbon dioxide monitoring tube forms a carbon dioxide monitoring lumen that extends from the proximal end of the nasal tube to an opening in the side of the nasal tube towards the distal end of the nasal tube. The nasal tube is configured such that the oxygen delivery and carbon dioxide monitoring lumens terminate at different levels relative to one another. With the oxygen delivery outlet positioned below the inlet of the carbon dioxide monitoring lumen, the delivered oxygen does not interfere with monitoring of returning carbon dioxide.

In certain embodiments, one or more tubes may be at least partially housed in a sheath to form a nasal tube device of the present application. For example, in one embodiment, a magnet delivery tube, an oxygen delivery tube, and a carbon dioxide monitoring tube are at least partially housed in a sheath to form a nasal tube device. The sheath may be configured in a variety of ways, such as, for example, a tubing or wrap that holds the one or more tubes together. In one embodiment, the sheath comprises heat shrink tubing.

Because certain nasal tube devices are configured to be used as dedicated anesthesiology monitoring/oxygen delivery device, they do not need to have large lumens configured to provide a patent airway for the patient. As such, the nasal tube may be smaller in diameter than other nasal tubes, thus reducing the amount of discomfort to the patient. Further, the nasal tube devices may be configured to provide a passive patent airway with the addition of an airway lumen or as a function of one or more of the lumens passing air when the nasal tube device is not hooked up to one or more monitoring machines.

The nasal tube devices may have a variety of cross sectional configurations. For example, the nasal tube may comprise three lumens and a delivery lumen for delivery of a connector and flexible line of the retention system. The delivery lumen may be circular in shape and completely surround the connector and line of the retention system. As such, the line is continuously secured to the nasal tube via the delivery lumen. However, in other embodiments, a slit or opening may exist between the delivery lumen and the outer surface of the nasal tube forming a channel for the connector and line of the retention system. As such, the line may escape the delivery lumen after placement such that retention of the nasal tube would be located at the clip/tube level. Further, in certain embodiments, the delivery lumen is a circular or non-circular delivery passage formed on or otherwise attached to the outer surface of the nasal tube.

Figure 9A:
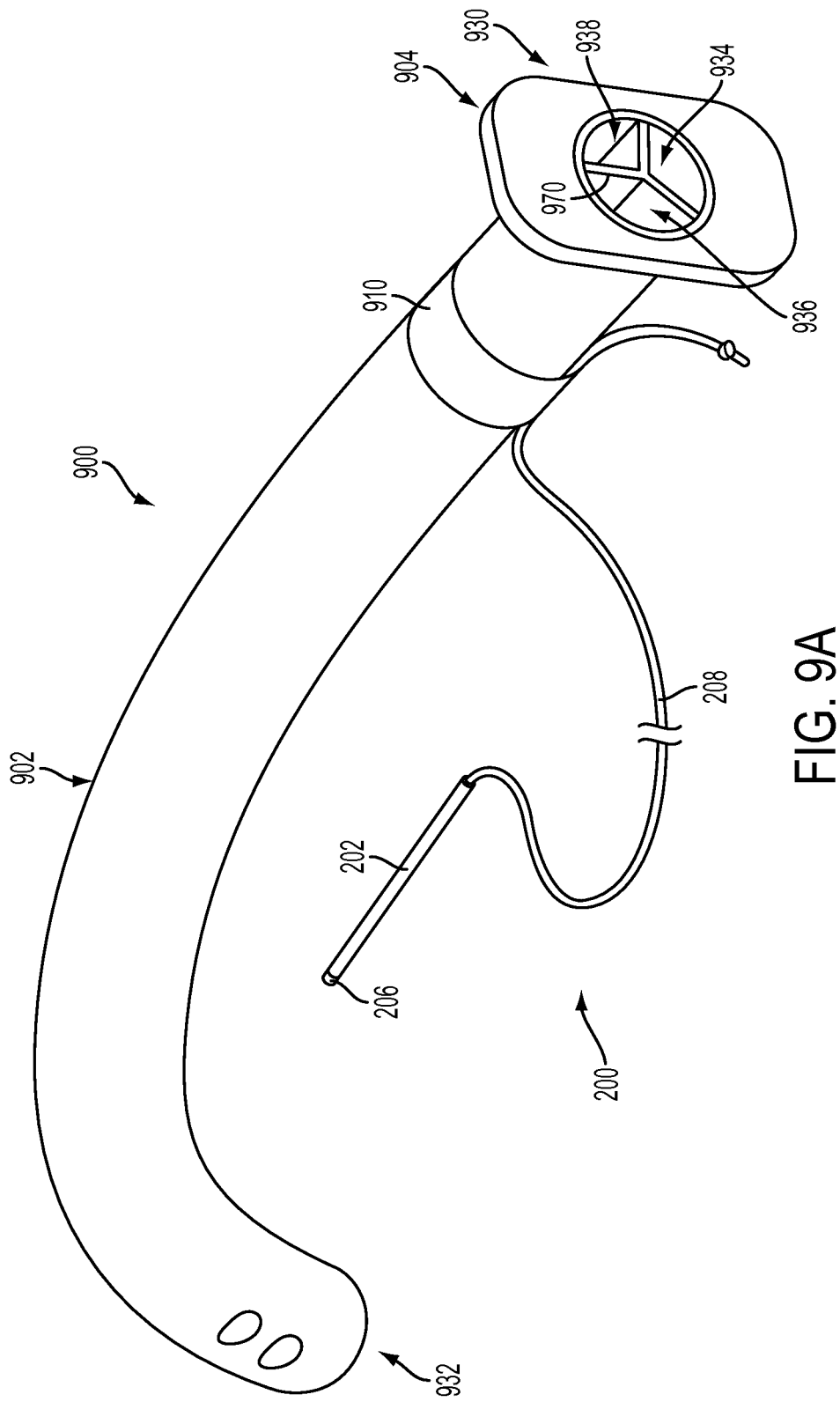
FIG. 9A is a perspective view of a nasal tube device according to an embodiment of the present application, wherein the nasal tube device is attached to a retention system according to an embodiment of the present application.
Figure 9B:
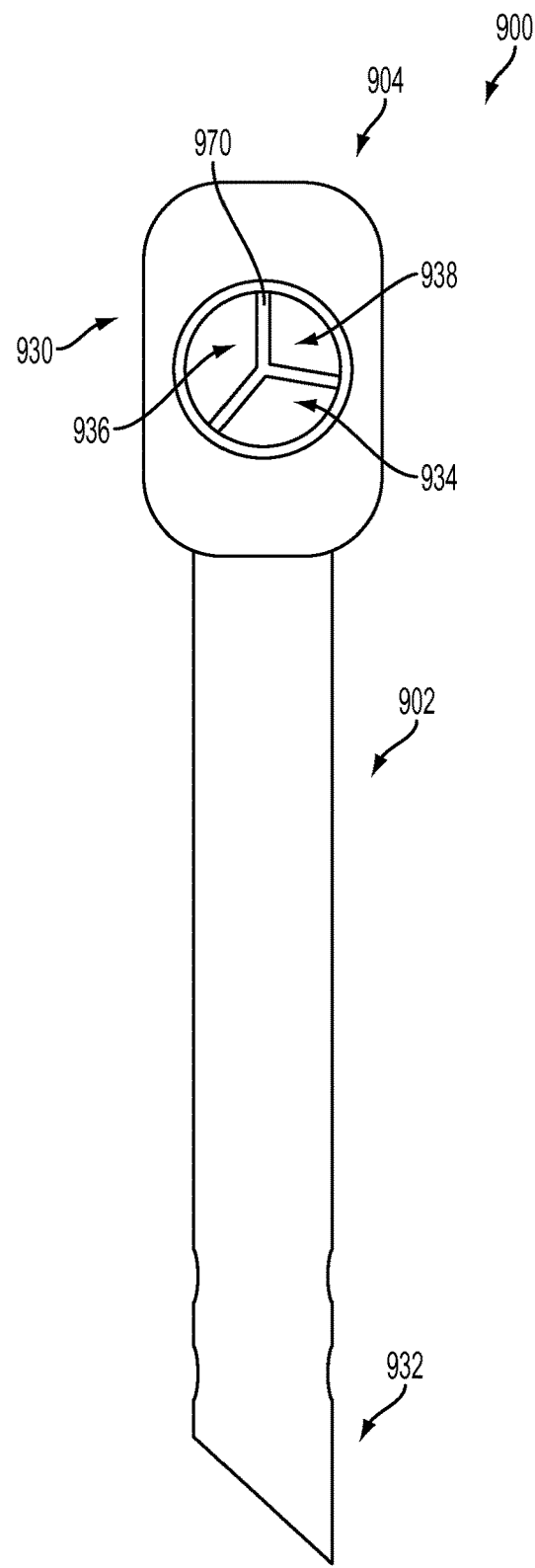
FIG. 9B is a front view of the nasal tube device of FIG. 9A.
Figure 10A:
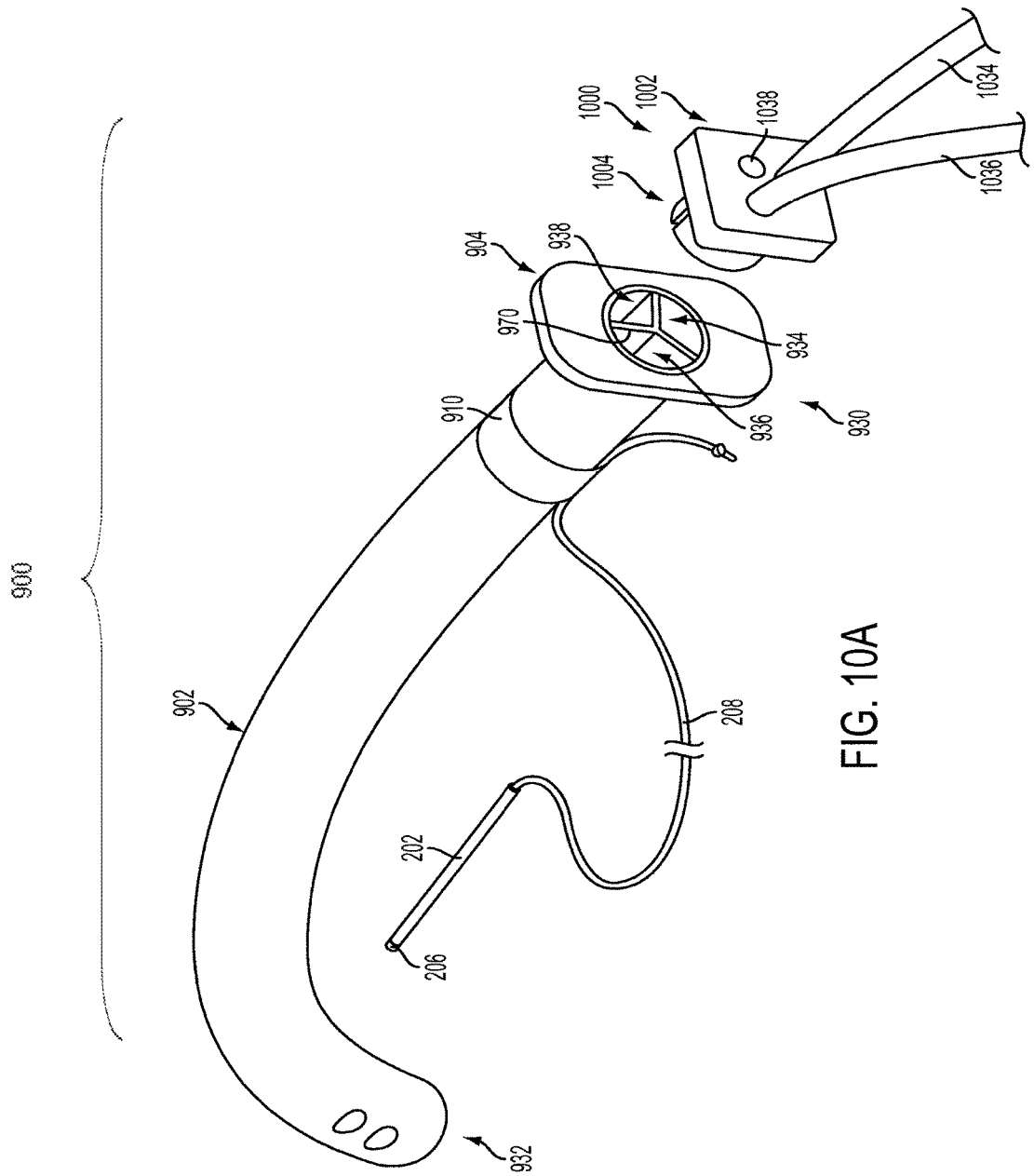
FIGS. 10A and 10B are perspective views of the nasal tube device of FIG. 9A illustrating the connection of the nasal tube device to an adapter according to an embodiment of the present application.
Figure 10B:
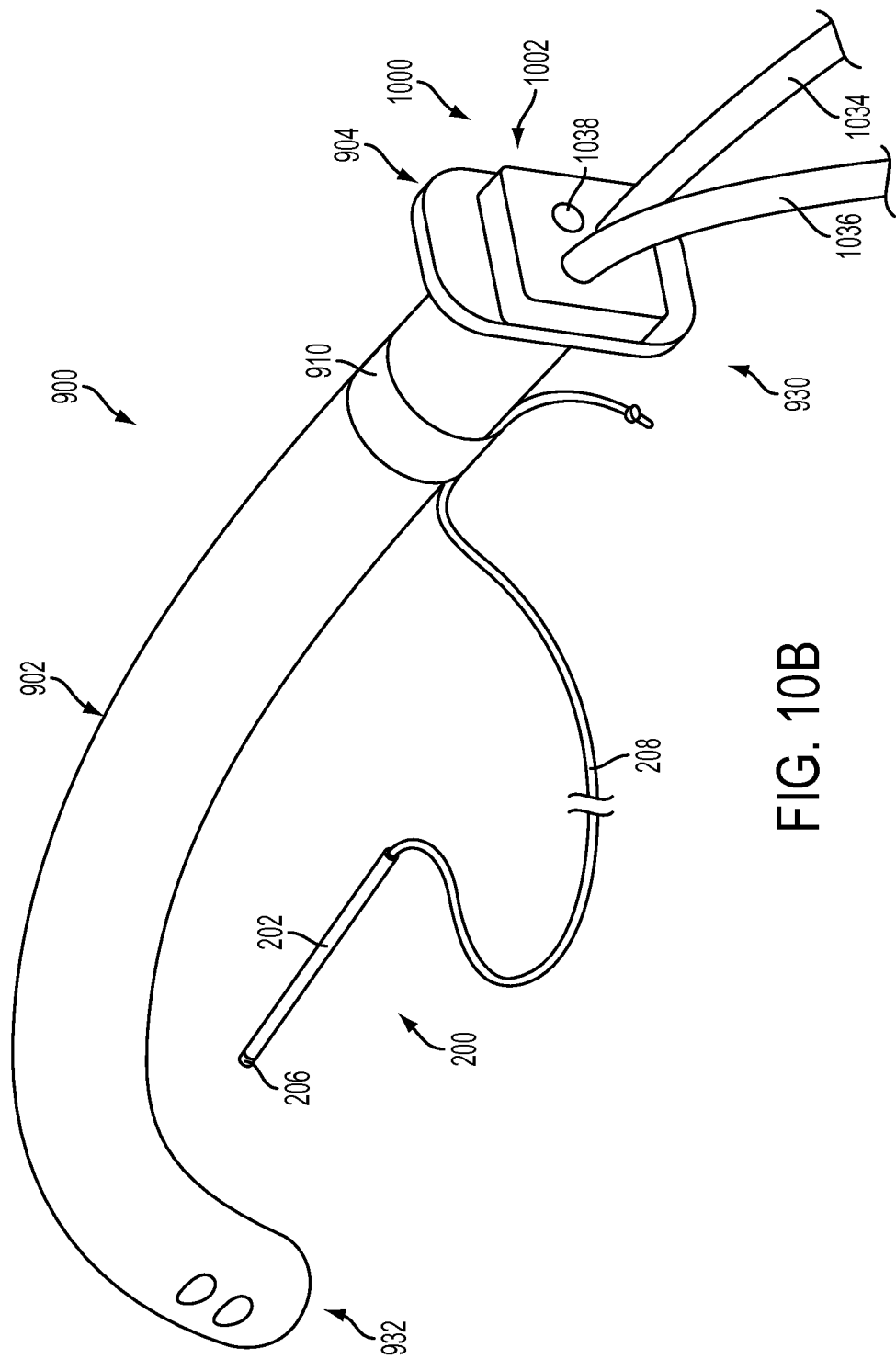

FIGS. 9A-10B illustrate a nasal tube device 900 according to an embodiment of the present application. The nasal tube device 900 comprises a nasal tube 902, a retention flange 904, and a securing device 910. The nasal tube 902 form the body of the device 900 and has a proximal end 930 and a distal end 932. As shown, the nasal tube 902 comprises three lumens extending from the proximal end 930 to the distal end 932 of the tube. However, in other embodiments, the nasal tube 902 may comprise more or less lumens, e.g., one, two, four or more lumens. Further, the nasal tube device 900 is shown in FIGS. 9A, 10A, and 10B attached to an exemplary retention system 200. The retention system 200 comprises the bridle line 208, catheter 202 having the first connector 206 (e.g., a magnet) at the distal end, and the connecting member (not shown) having the second connector (e.g., a magnet) at the distal end. The bridle line 208 is attached to the catheter 202 and the nasal tube device 900 with the securing device 910.

As illustrated in FIGS. 9A-10B, the securing device 910 comprises a piece of heat shrink tubing that attaches the bridle line 208 to the nasal tube 902. However, the bridle line 208 may be attached to the nasal tube 902 in a variety of other ways. For example, the bridle line 208 may be threaded through an opening in the retention flange 904 and may be knotted to prohibit removal of the line from the nasal tube 902. The bridle line 208 may also be attached to the nasal tube 902 by threading the line through a hole in the nasal tube and knotting an end of the line to prohibit removal of the line from the nasal tube. Further, the bridle line 208 may be attached to the nasal tube 902 with one or more ties, elastic bands, tape, glue or other adhesive, clips or other fasteners or retainers. For example, the bridle line 208 may be attached to the nasal tube 902 with an adhesive, with or without the heat shrink tubing. Further, the bridle line 208 may be attached to one or more tubes extending from the lumens of the nasal tube 902, such as, for example, oxygen and carbon dioxide tubes (e.g., with a clip, adhesive and/or heat shrink tubing). The bridle line 208 may also be overmolded with the nasal tube 902 to attach the line to the nasal tube device 900.

The multiple lumens of the nasal tube device 900 may be used for a variety of purposes. As illustrated in FIGS. 9A-10B, the nasal tube 902 comprises a first lumen 934, second lumen 936, and third lumen 938. The first lumen 934 and the second lumen 936 of the nasal tube 902 segregate gases such as carbon dioxide and oxygen, respectively, that permit the nasal tube device 900 to act as an anesthesia monitoring aid for conscious sedation procedures and a secure passive airway adjunct for perioperative monitoring and continuous airway protection. The third lumen 938 is auxiliary and serves as a port for the introduction of instruments such as but not limited to suction catheters or video equipment. Further, one or more lumens of the nasal tube may be configured as a delivery lumen for a connector the retention system.

One exemplary method of placing and securing the nasal tube device 900 to a patient includes inserting the distal end of the catheter 202 into a first nostril of the patient and the distal end of the connecting member into a second nostril of the patient. The distal ends of the catheter 202 and the connecting member are advanced into the nasopharnyx 304 (FIG. 3). The first connector 206 of the catheter 202 meets the second connector of the connecting member in the nasopharnyx 304 to establish a connection. In certain embodiments, the first and second connectors are magnets that attach together when placed in proximity to one another. Once connected, the connecting member is retracted out of the second nostril. Retraction of the connecting member pulls the catheter 202 and the bridle line 208 around the posterior free edge of the vomer 302 (FIG. 3). As the catheter 202 and the bridle line 208 are wrapped around the vomer 302, the nasal tube 902 is advanced into the first nostril of the patient and positioned such that the distal end 932 of the nasal tube terminates in a pharyngeal space of the patient.

The portions of the bridle line 208 extending from the nostrils may be tied together or attached in a variety of ways, such as for example, with one or more ties, elastic bands, tape, adhesive, heat shrink tubing, clips or other fasteners or retainers. The portions of the bridle line 208 may also be attached or otherwise secured to the nasal tube 902 or components attached to the nasal tube, such as for example, anesthesia lines connected to the nasal tube. For example, the portions of the bridle line 208 may be attached to one or more tubes extending from the nasal tube 902, such as, for example, oxygen and carbon dioxide tubes, with a clip. As another example, the portions of the bridle line 208 may be attached together exterior to the nose with a clip.

The nasal tube device 900 eliminates a step in the overall placement and securement procedure for the nasal tube 902. For example, when a separate nasal tube and nasal tube retention system is used, the bridle line of the retention system is first routed around the vomer of the patient and then the nasal tube is placed over the bridle line. If adequate tension is not maintained on the bridle line during placement of the nasal tube, the line may become dislodged or pulled out of position. The nasal tube device 900 eliminates this step of placing the nasal tube over the bridle line.

The nasal tube device of the present application may comprise one or more adapters or connectors that facilitate connection of various components or equipment to the nasal tube, such as, for example, one or more anesthesia lines or other respiratory related equipment, such as a bag valve mask. The adaptor or connector may be inserted into an end of the nasal tube (e.g., in one or more lumens of the nasal tube) and/or attached to the nasal tube, such as around the circumference of the nasal tube, to a flange of the nasal tube, etc. The adapter or connector may be removable, non-removable or integrally formed with the nasal tube and may or may not comprise a flange portion. The adapter or connector may be connected to the nasal tube in a variety of ways, such as for example, with an interference fit, slip fit, barbed fitting, locking mechanism, clip, bonded or molded insert, or other fastener.

Figure 11:
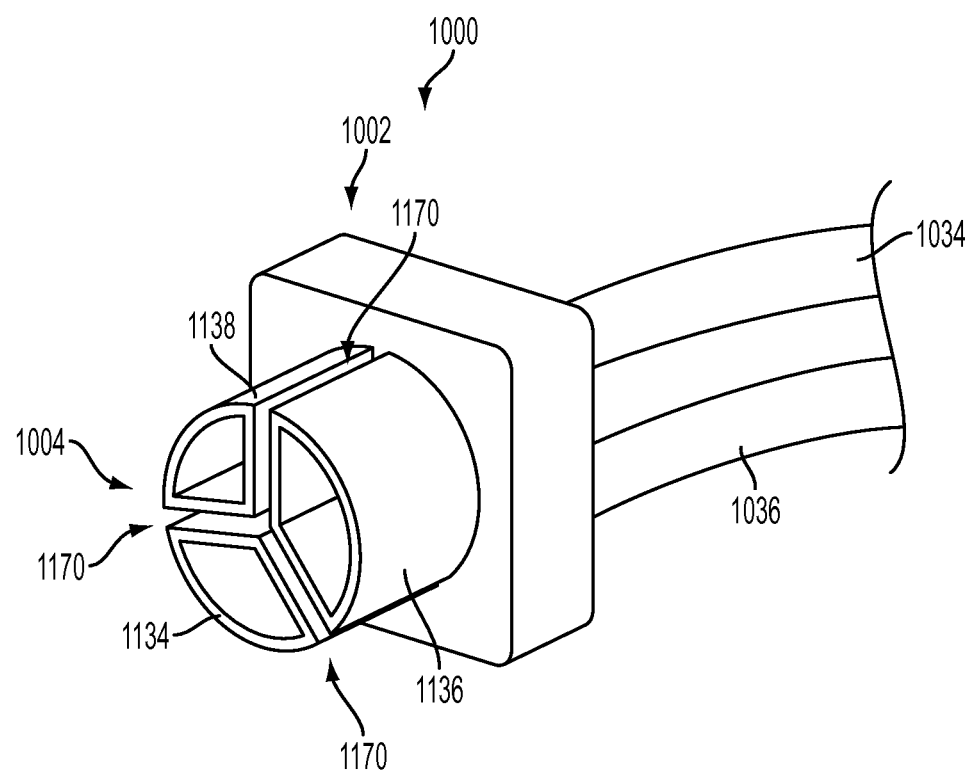
FIG. 11 is a perspective view of an adapter according to an embodiment of the present application.

FIG. 11 illustrates an adapter 1000 according to an exemplary embodiment of the present application and FIGS. 10A and 10B illustrate the adapter 1000 being attached or connected to the nasal tube device 900. As shown in the FIGS. 10A-11, a first end 1004 of the adapter 1000 comprises a first port 1134, a second port 1136, and a third port 1138 having outer walls that are shaped and configured to be received in the first lumen 934, second lumen 936, and third lumen 938, respectively, of the nasal tube 902. As such, the first port 1134 is in fluid communication with the first lumen 934, the second port 1136 is in fluid communication with the second lumen 936, and the third port 1138 is in fluid communication with the third lumen 938 when the adapter 1000 is inserted into the nasal tube 902. The outer walls of the ports 1134, 1136, and 1138 of the adapter 1000 are shaped and configured to provide an interference fit with the lumens 934, 936, and 938 of the nasal tube 902. As such, adapter 1000 may be easily and quickly removed from the nasal tube 902. Further, the interference fit provides a fluid tight connection between the ports 1134, 1136, and 1138 of the adapter 1000 and the lumens 934, 936, and 938 of the nasal tube 902. In other embodiments, the adapter may comprise more or less ports shaped and configured to be received in more or less lumens of the nasal tube.

As illustrated in FIG. 11, the adapter 1000 comprises a slots or spaces 1170 dividing the ports 1134, 1136, and 1138 that facilitate insertion of the adapter into the lumens 934, 936, and 938 of the nasal tube 902. For example, as illustrated in FIGS. 10A and 10B, when the first end 1004 of the adapter 1000 is inserted into the lumens 934, 936, and 938 of the nasal tube 902, the spaces 1170 dividing the ports 1134, 1136, and 1138 are aligned with the walls 970 dividing the lumens. The adapter 1000 may be inserted into the nasal tube 902 until the body of the adapter and/or the end wall of the spaces 1170 abuts the walls 970 dividing the lumens 934, 936, and 938.

As illustrated in FIGS. 10A and 10B, a second end 1002 of the adapter 1000 comprises ports in fluid communication with the ports 1134, 1136, and 1138 of the first end 1004. As shown, the first and second ports of the second end 1002 are configured for removable connection to anesthesia lines 1034 and 1036, respectively. More specifically, a carbon dioxide line 1034 and an oxygen line 1036 are removably connected to the first and second ports, respectively, of the second end 1002 of the adapter 1000. As such, the carbon dioxide line 1034 is fluidly connected to the first lumen 934 and the oxygen line 1036 is fluidly connected to the second lumen 936 of the nasal tube 902. However, the adapter 900 may not be limited to the connection of anesthesia related equipment, but may also, for example, accept positive pressure ventilation systems and may comprise one or more valves in such cases.

As illustrated in FIGS. 10A and 10B, the second 1002 of the adapter 1000 comprises a third or auxiliary port 1038 that communicates with the third port 1138 of the first end 1004. Further, the auxiliary port 1038 communicates with the third lumen 938 of the nasal tube 902. In certain embodiments, the auxiliary port 1038 is used to introduce instruments, such as, for example, suction catheters or video equipment, into the third lumen 938 of the nasal tube 902.

In certain embodiments, the adapter comprises only the first and second ports for fluidly connecting anesthesia lines 1034 and 1036 to first and second lumens 934 and 936 of the nasal tube 902. Further, in one embodiment, at least a portion of the second end of the two port adapter extends at an angle relative to the first end, e.g., up and away from the first end. As such, the orientation of the second end relative to the first end permits access to the third lumen 938 of the nasal tube 902. As such, the third lumen 938 is not blocked by the adapter, for example the third lumen may still be used to introduce tools such as suction catheters or video equipment.

Further, in certain embodiments, the nasal tube device of the present application may comprise connectors for attaching one or more tubes directly to the nasal tube (e.g., at the proximal end of the nasal tube or nare of the nose when the nasal tube is inserted). For example, one or more luer connectors may be used to attach the one or more tubes to the nasal tube. Male luer connectors may be attached to the lumens of the nasal tube and the mating female luer connectors may be attached to the ends of the one or more tubes. Further, in certain embodiments, the one or more tubes may be attached to the lumens of the nasal tube with a friction fit. Further, the one or more tubes may comprise barbed connectors configured to attach to the lumens of the nasal tube. For example, one or more lumens of the nasal tube may comprise barbs for attachment of the one or more tubes.

Figure 12A:
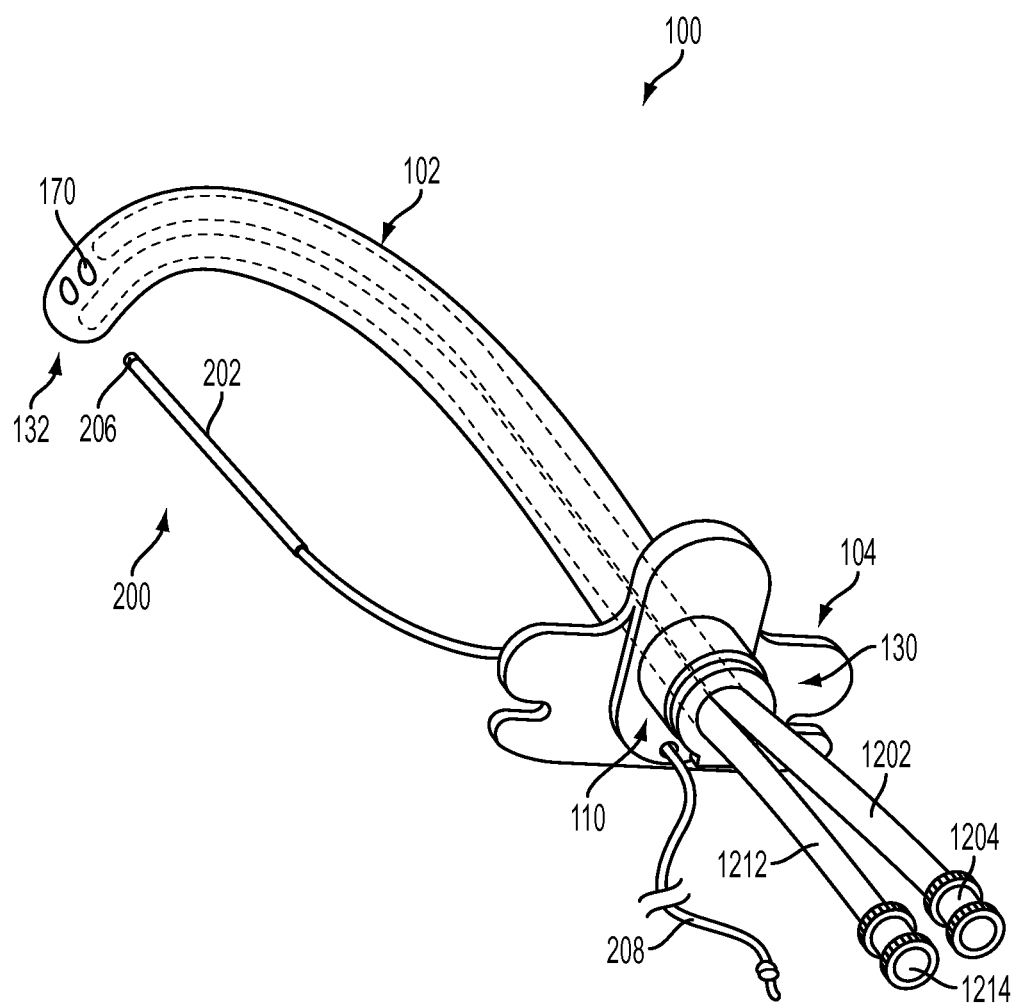
FIG. 12A is a perspective view of the nasal tube device of FIG. 1A, wherein the nasal tube device is preloaded with medical tubes according to an embodiment of the present application.
Figure 12B:
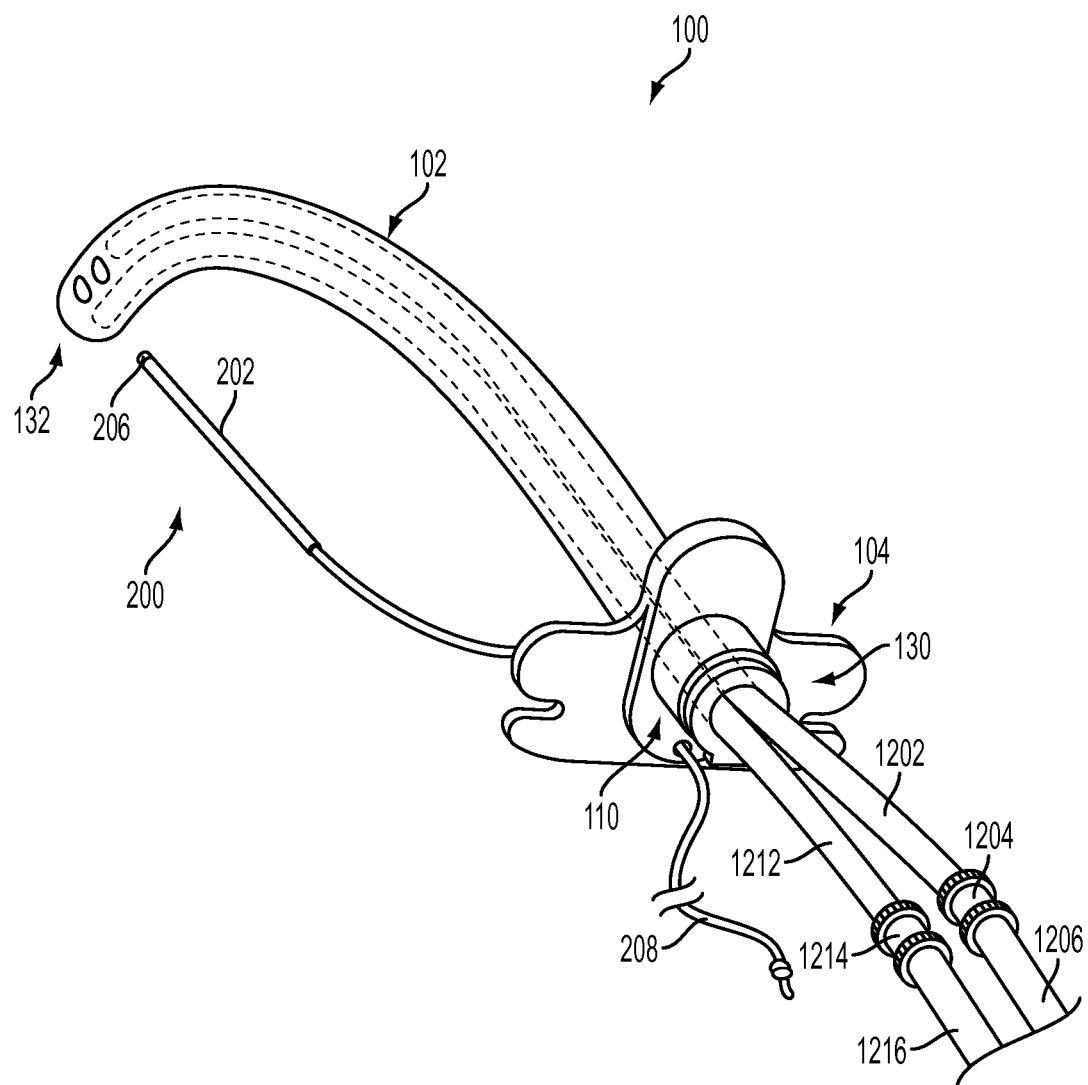
FIG. 12B is a perspective view of the nasal tube device of FIG. 12A, wherein the preloaded medical tubes are attached to external tubes according to an embodiment of the present application.
Figure 13:
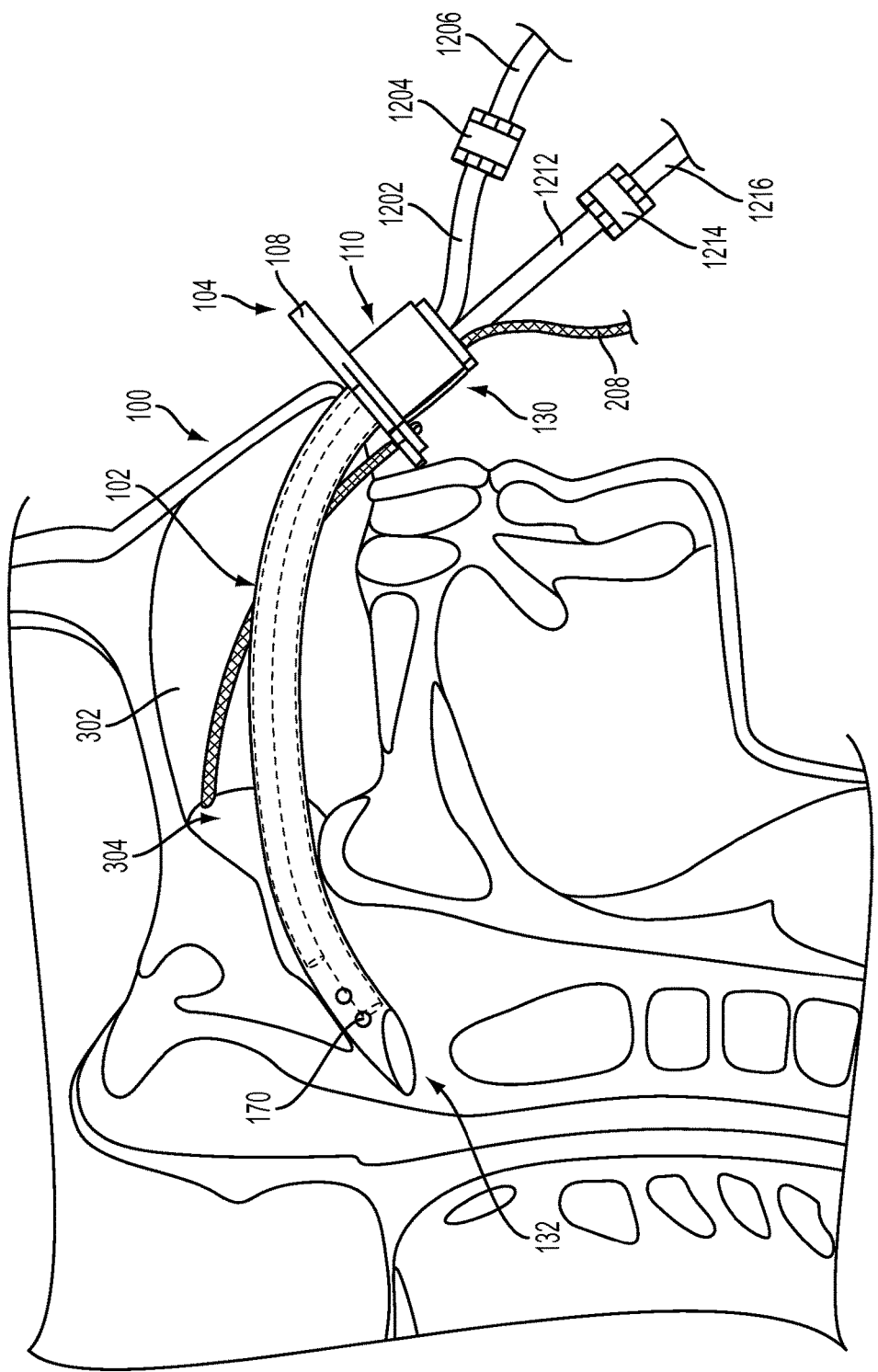
FIG. 13 is a partial cross sectional view of the nasal tube device of FIG. 12B, wherein the nasal tube device is positioned in a patient.

FIGS. 12A-13 illustrate the nasal tube device 100 with preloaded medical tubes 1202 and 1212. As such, the preloaded medical tubes 1202 and 1212 are placed inside the lumen of the nasal tube 102 and secured prior to placement of the nasal tube on the patient and/or securement of the nasal tube device 100 to the patient.

As illustrated in FIGS. 12A-13, the nasal tube device 100 comprises a carbon dioxide monitoring tube 1202 and an oxygen delivery tube 1212 secured within the lumen of the nasal tube 102 with the securing device 110. The carbon dioxide monitoring tube 1202 and the oxygen delivery tube 1212 each comprise connectors 1204 and 1214 for removably connecting an external monitoring tube 1206 and an external delivery tube 1216 to the preloaded tubes, as illustrated in FIGS. 12B and 13. However, it should be understood that the nasal tube device 100 may comprise a variety of preloaded medical tubes and is not limited to the connection of anesthesia related equipment, but may also, for example, accept positive pressure ventilation systems and may comprise one or more valves in such cases. Further, the connectors of the present application may be adapted to attach to other respiratory related equipment, such as, for example, a bag valve mask.

Further, as illustrated in FIGS. 12A-13, the oxygen delivery tube 1212 and the carbon dioxide monitoring tube 1202 are positioned in the nasal tube 102 such that they terminate at different body levels relative to one another. Terminating the outlet of the oxygen delivery tube 1212 and the inlet of the carbon dioxide monitoring tube 1202 at different levels reduces the risk that the delivered oxygen will interfere with monitoring of returning carbon dioxide. As shown, the outlet of the oxygen delivery tube 1212 is positioned below the inlet of the carbon dioxide monitoring tube 1202.

As illustrated in FIGS. 12A-13, the nasal tube device 100 is configured to be used as an oxygen delivery and/or carbon dioxide monitoring aid to support anesthesiology activities. The oxygen delivery tube 1212 and/or the carbon dioxide sampling tube 1202 may be preloaded into the main lumen of the nasal tube device 100 and secured to the device using the securing device 110. The oxygen tube 1212 and the carbon dioxide tube 1202 may also be adjusted relative to one another to optimize oxygen delivery and carbon dioxide sampling by use of the securing device 110 and its ability to open and lock repeatedly. In certain embodiments, one or more oxygen delivery tubes and/or one or more carbon dioxide monitoring tubes may securely interface with the nasal tube device 100 using the mechanisms described above. Further, in certain embodiments, one or more medical tubes, wires, and/or medical instruments may be preloaded inside the lumen of the nasal tube 102 and secured prior to placement of the nasal tube 102 on the patient and/or securement of the nasal tube device 100 to the patient. The securing device 110 also permits the preloaded medical tubes, wires, and/or medical instruments to be quickly removed such that the nasal tube device 100 may be used to securely protect a patent airway in a similar fashion to a traditional nasopharyngeal airway device.

A wide variety of connectors may be used to connect the one or more external tubes to one or more tubes extending from the nasal tube 102. Further, in certain embodiments, the connectors may be adapted to attach to other respiratory related equipment, such as, for example, a bag valve mask. As illustrated in FIGS. 12A-13, the connectors 1204 and 1214 are luer connectors configured to attach the external tubes 1206 and 1216 to the tubes 1202 and 1212 extending from the nasal tube 102. In certain embodiments, molded connectors may be attached to the ends of the tubes extending from the nasal tube (e.g., with a friction fit or adhesive). The molded connectors may comprise ports for attachment to the one or more external tubes. Further, barbed connectors may be used to attach the one or more external tubes to the one or more tubes extending from the nasal tube.

The nasal tubes of the present application are sufficiently strong and flexible to penult advancement and placement of the tube in the patient and prohibit undesirable collapse or compression of the tube under pressure imparted by the patient's anatomical structures. Further, the nasal tubes of the present application are sufficiently flexible such that the tube may be bent or otherwise manipulated during advancement and placement, such as for example, when the tube dives from the nasopharyngeal into the oropharyngeal space. Further, the exterior of the nasal tube may be soft to protect the delicate and vasoactive nasal mucosa and epithelium.

The nasal tubes of the present application may comprise a variety of materials. For example, many moldable polymers may be used for the nasal tube, such as silicone, polyvinyl chloride (PVC), block co-polymers, other thermoplastic elastomers, and natural rubber. These polymers generally possess the physical properties and biocompatible characteristics needed for the nasal tubes for the present application. Further, the polymer material of the nasal tube may have a high melt temperature and/or electrical insulating characteristics. For example, in some embodiments, the nasal tube comprises silicone to aid in the prevention of nasal airway fires during electrosurgical procedures of the head and neck. Silicone has no melting point. Silicone's tolerance to high heat may add additional patient and caregiver protection in the event of an operating room fire. Moreover, silicone will not melt which adds protection from tube melt blockages and associated tissue damage as the tube's material responds to the intense thermal exposure during operating room fires. Further, the nasal tube devices of the present application segregate and sequester gases, especially oxygen, and controls them until they are out of reach of surface electrosurgical arcing and ignition surfaces.

The nasal tubes of the present application may be various lengths and diameters to accommodate different sized patient anatomies. Further, the cross section of the nasal tube may be a variety of sizes and shapes and may or may not be uniform along the length of the nasal tube. For example, the cross section of the nasal tube may be circular, ovoid, elliptical, oval, or other non-circular shapes. Various non-circular shapes may provide stability for ease of insertion and compliance with regard to the nasal anatomy and long-term retention. Further, the nasal tubes of the present application may be curved along the longitudinal axis to mimic the anatomy of the patient and aid in directing the distal end of the tube during insertion at the posterior nasopharnyx. The proximal end of the nasal tube may also have a slight flare to accommodate adapters and function as an anchor point for the retention system.

The nasal tube or nasal retention system components may also comprise indicators or graduations along its length to facilitate proper alignment and estimation of the nasal tube position within the nose, such as for example, the position of the delivery window. The exterior of the nasal tube and/or the retention system components may also comprise drug treatments such as but not limited to anti-bacterial, vasoactive, analgesic agents or combinations of drugs. The exterior may also include surface treatments for hydrophilicity, hydrophobicity, and/or lubricious treatments to aid in insertion of device. The lubricious and/or drug treatments may be packaged with a breakable liquid pouch to immediately activate the surface treatments. Further, the external surface of the nasal tube may be textured along its longitudinal axis or morphologically incongruent to aid in tube insertion and rotational stability as the tube navigates through the nasal passage and levels of the nasal choanae. The nasal tubes of the present application may also comprise holes or other perforations along the length of the tube to permit the directed exchange of gases. Additionally, the tube exterior may comprise closed cell foam or anticoagulant packing. The exterior of the nasal tube may also comprise coatings or surface treatments that expand, swell, bulge, or otherwise increase the outer size of the nasal tube in the presence of moisture. As such, the expanded portion of the nasal tube may act as an anchor and increase the friction between the nasal tube and the patient to facilitate retention of the tube in the patient. Further, the expanded portion of the tube may act as packing for hemostatis purposes, such as to decrease or prohibit nasal bleeding.

In certain embodiments, the nasal tube device of the present application may comprise one or more sensors disposed in a lumen of the nasal tube or on the surface of the nasal tube. The sensors may be used to monitor various physiological conditions of the patient. For example, a pulse oximeter or other monitoring sensor may be disposed in one or more lumens of the nasal tube or on the surface of the nasal tube. Further, wires attached to the sensor may be routed through the lumen of the nasal tube and back out of the nasal tube device. The monitoring sensors may also be incorporated onto the exterior of the nasal tube device or disposed within one or more lumens of the nasal tube device. Various types of monitoring sensors may include electrodes for heart rate, temperature sensors, pulse oximeters, EKG, etc.

Figure 14:
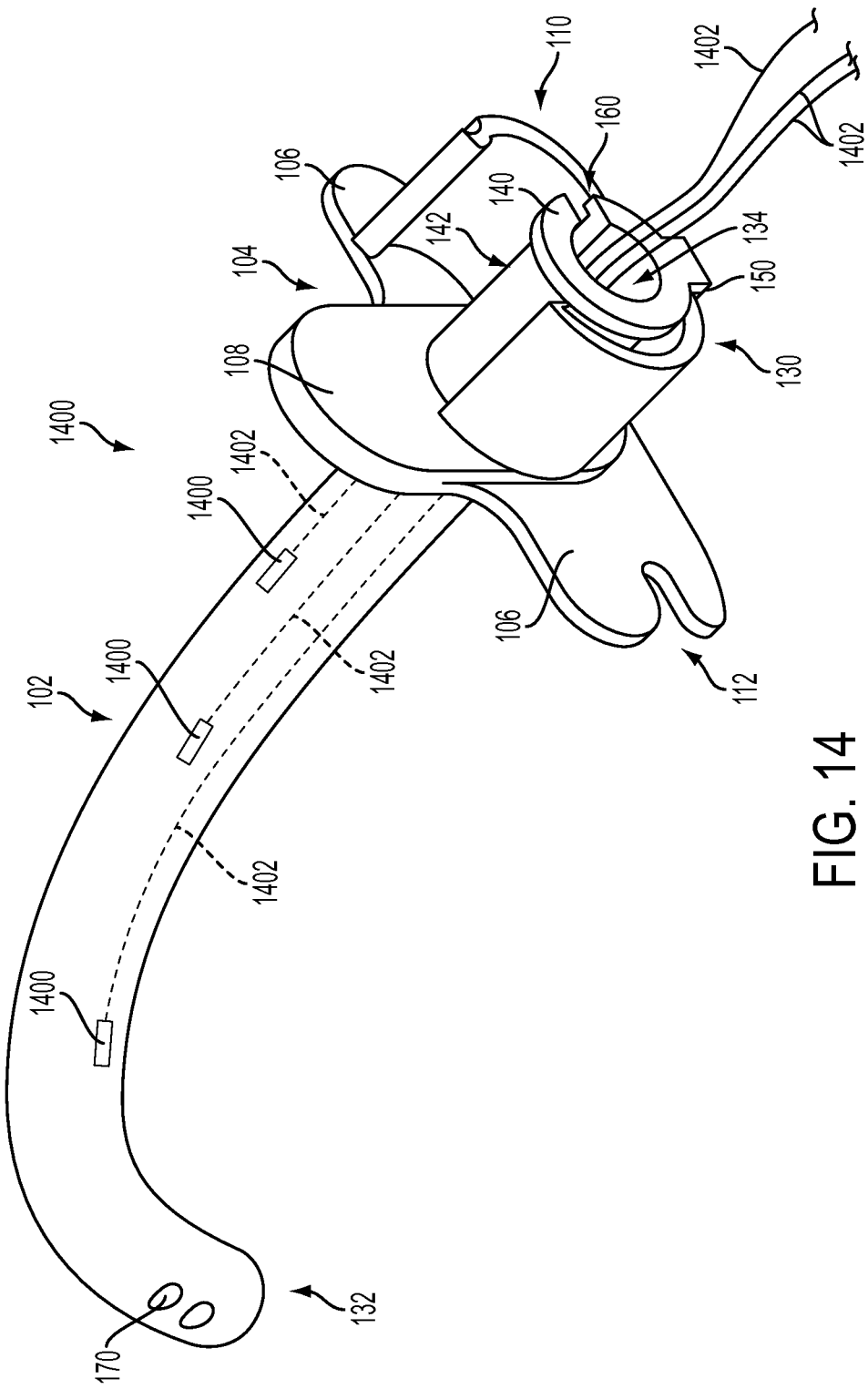
FIG. 14 is a perspective view of a nasal tube device according to an embodiment of the present application.

For example, FIG. 14 illustrates a nasal tube device 1400 according to an embodiment of the present application. As shown, the nasal tube device 1400 comprises a plurality of the sensors 1400 disposed on the surface of the nasal tube 102. The sensors 1400 may be attached to the surface or integrated into the nasal tube 102 in a variety of ways, such as, for example, with a friction fit (e.g., disposed in an opening or slit in the nasal tube), one or more fasteners, adhesive, tape, elastic band, weld, overmold, etc. Wires 1402 attached to the sensors 1400 are routed through the lumen 134 of the nasal tube 102 and out of the nasal tube device 1400 for connection to one or more pieces of monitoring equipment. Similar to the bridle line 208 and medical tubes described above, the wires 1402 may be secured to the nasal tube 102 when the securing device 110 is closed. The sensors 1400 may be various types of patient monitoring sensors, including but not limited to heart rate sensors, temperature sensors, pulse oximeters, EKG, carbon dioxide or oxygen sensors, etc. As shown, the sensors 1400 are disposed at various locations on the nasal tube 102 and at various distances from the proximal end 130 of the nasal tube. As such, one or more of the sensors 1400 may be positioned to monitor the patient at various body levels. In certain embodiments, one or more of the sensors 1400 may be disposed in the lumen 134 or incorporated onto the exterior of the nasal tube device and the wires may or may not be routed through the lumen. Further, the sensors 1400 may be wireless and capable communicating remotely with one or more pieces of monitoring equipment.

As described herein, when one or more components are described as being connected, joined, affixed, coupled, attached, or otherwise interconnected, such interconnection may be direct as between the components or may be in direct such as through the use of one or more intermediary components. Also as described herein, reference to a "member,"

"component," or "portion" shall not be limited to a single structural member, component, or element but can include an assembly of components, members or elements.

While the present invention has been illustrated by the description of embodiments thereof, and while the embodiments have been described in considerable detail, it is not the intention of the applicants to restrict or in any way limit the scope of the invention to such details. Additional advantages and modifications will readily appear to those skilled in the art. For example, where components are releasably or removably connected or attached together, any type of releasable connection may be suitable including for example, locking connections, fastened connections, tongue and groove connections, etc. Still further, component geometries, shapes, and dimensions can be modified without changing the overall role or function of the components. Therefore, the inventive concept, in its broader aspects, is not limited to the specific details, the representative apparatus, and illustrative examples shown and described. Accordingly, departures may be made from such details without departing from the spirit or scope of the applicant's general inventive concept.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure, however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

We claim:

1. A nasal tube system comprising: a nasal tube, the nasal tube comprising:
    a first opening at a proximal end;
    a second opening at a distal end;
    a delivery window between the proximal end and the distal end and in an outer surface of the nasal tube;
    a main lumen extending an entire length of the nasal tube from the first opening to the second opening;
    a delivery lumen extending from the first opening to the delivery window; and
    a wall at least partially separating and defining the main lumen and the delivery lumen,
    wherein the nasal tube is configured to be inserted into a first nostril of a patient with the proximal end and the first opening positioned outside of the patient, and the second opening and the delivery window open to pharyngeal space of the patient; and a flexible line that secures the nasal tube to the patient by extending through the delivery lumen and the delivery window of the nasal tube.

2. The nasal tube system of claim 1, wherein
    the flexible line extends through delivery lumen of the nasal tube, out of the nasal tube through the delivery window, around the patient's vomer bone, and is secured at the proximal end of the nasal tube positioned outside of the patient.

3. The nasal tube system of claim 2, further comprising a retention flange having an opening configured to attach the flexible line to the nasal tube ice.

4. The nasal tube system of claim 2, further comprising a retention flange having a tab portion extending from a central portion, wherein the tab portion is configured to guide the flexible line.

5. The nasal tube system of claim 2, further comprising a securing device attached to the proximal end of the nasal tube outside of the patient, wherein the securing device is configured to attach the flexible line to the proximal end of the nasal tube outside of the patient.

6. The nasal tube system of claim 5, wherein the securing device is configured to compress the proximal end of the nasal tube positioned outside of the patient.

7. The nasal tube system of claim 6, wherein compression of the securing device is configured to secure a medical tube disposed in the main lumen of the nasal tube.

8. The nasal tube system of claim 5, further comprising a retaining strap configured to prohibit removal of the securing device from the nasal tube.

9. The nasal tube system claim 5, wherein the securing device is a clip that substantially surrounds the proximal end of the nasal tube outside of the patient when the securing device is in a closed position.

10. The nasal tube system of claim 9, wherein the clip comprises a living hinge and a locking mechanism, wherein the living hinge comprises a depression for facilitating movement of the clip between an open position and the closed position.

11. The nasal tube system of claim 10, wherein the locking mechanism of the clip is a tongue and groove locking mechanism.

12. The nasal tube system of claim 5, further comprising a retention flange, wherein the securing device is disposed in a recessed portion of the nasal tube located between the retention flange and the proximal end of the nasal tube.

13. The nasal tube system of claim 2, further comprising a securing device movable between an open position and a closed position, wherein the securing device is attached to the proximal end of the nasal tube positioned outside of the patient.

14. The nasal tube system of claim 13, wherein the securing device is configured to removably attach the flexible line to the proximal end of the nasal tube positioned outside of the patient.

15. The nasal tube system of claim 13, further comprising a medical tube disposed in the main lumen of the nasal tube,
   wherein the medical tube extends from the first opening through the main lumen of the nasal tube, and
   wherein the securing device is configured to secure the medical tubes to the proximal end positioned outside the patient when the securing device is in the closed position.

16. The nasal tube system of claim 15, wherein the medical tube comprises one or more connectors for attaching the medical tube to one or more external tubes.

17. The nasal tube system of claim 15, wherein the medical tube comprises an oxygen delivery tube and a carbon dioxide monitoring tube, and wherein the oxygen delivery tube and the carbon dioxide monitoring tube are positioned in the at main lumen such that oxygen delivery tube and the carbon dioxide monitoring tube terminate at different body levels relative to one another.

18. The nasal tube system of claim 1, wherein the delivery window is located at a position between the proximal end and the distal end such that when the nasal tube is inserted into the first nostril of a patient and is secured to the patient, the delivery window is located proximate the patient's vomer bone.

19. The nasal tube system of claim 1, further comprising one or more sensors disposed on an outer surface of the nasal tube.

20. The nasal tube system of claim 19, wherein the one or more sensors include an oxygen sensor and a carbon dioxide sensor.

21. The nasal tube system of claim 20, wherein the one or more sensors are positioned to monitor a user at various body levels.

22. The nasal tube system of claim 19, wherein the one or more sensors are configured to monitor various physiological conditions of a user.

* * * * *